(12) United States Patent
Wang

(10) Patent No.: US 11,028,184 B2
(45) Date of Patent: Jun. 8, 2021

(54) LONG-ACTING PCSK9-SPECIFIC BINDING PROTEIN AND APPLICATION THEREOF

(71) Applicant: CHANGZHOU BOJIA BIOTECHNOLOGY CO., LTD, Jiangsu (CN)

(72) Inventor: Shaoxiong Wang, Shanghai (CN)

(73) Assignee: CHANGZHOU BOJIA BIOTECHNOLOGY CO., LTD, Jiangsu (CN)

( * ) Notice: Subject to any disclaimer, the term of this patent is extended or adjusted under 35 U.S.C. 154(b) by 0 days.

(21) Appl. No.: 16/308,811

(22) PCT Filed: Jun. 8, 2017

(86) PCT No.: PCT/CN2017/087536
§ 371 (c)(1),
(2) Date: Dec. 10, 2018

(87) PCT Pub. No.: WO2017/211313
PCT Pub. Date: Dec. 14, 2017

(65) Prior Publication Data
US 2019/0194356 A1   Jun. 27, 2019

(30) Foreign Application Priority Data
Jun. 8, 2016   (CN) .......................... 201610405036.7

(51) Int. Cl.
| | | |
|---|---|---|
| *A61K 39/395* | (2006.01) | |
| *C07K 16/18* | (2006.01) | |
| *C07K 16/40* | (2006.01) | |
| *A61P 3/06* | (2006.01) | |
| *C12N 9/64* | (2006.01) | |
| *C12N 15/62* | (2006.01) | |
| *G01N 33/58* | (2006.01) | |
| *A61K 38/00* | (2006.01) | |

(52) U.S. Cl.
CPC ............ *C07K 16/40* (2013.01); *A61K 39/395* (2013.01); *A61P 3/06* (2018.01); *C12N 9/6424* (2013.01); *C12N 15/62* (2013.01); *C12Y 304/21061* (2013.01); *G01N 33/582* (2013.01); *G01N 33/583* (2013.01); *A61K 38/00* (2013.01); *C07K 2317/32* (2013.01); *C07K 2317/565* (2013.01); *C07K 2319/30* (2013.01)

(58) Field of Classification Search
None
See application file for complete search history.

(56) References Cited

FOREIGN PATENT DOCUMENTS

| | | |
|---|---|---|
| CN | 101939338 | 1/2011 |
| CN | 102245641 | 11/2011 |
| CN | 104364266 | 2/2015 |
| CN | 105461809 | 4/2016 |
| WO | 2009100318 | 8/2009 |
| WO | 2010077854 | 7/2010 |
| WO | 2015/00438 | 12/2012 |
| WO | 2013169886 | 11/2013 |
| WO | 2013188855 | 12/2013 |
| WO | 2014/107739 | 7/2014 |

OTHER PUBLICATIONS

PCT: International Search Report of International Search Authority (Chinese Patent Office) dated Aug. 22, 2017 in PCT Application No. PCT/CN2017/087536 (With English Translation).
PCT: Written Opinion of International Search Authority (Chinese Patent Office) dated Aug. 22, 2017 in PCT Application No. PCT/CN2017/087536 (With English Translation).

*Primary Examiner* — Christine J Saoud
*Assistant Examiner* — Jon M Lockard
(74) *Attorney, Agent, or Firm* — Snell & Wilmer L.L.P.

(57) ABSTRACT

Provided is a long-acting PCSK9-specific binding protein and application thereof. Provided is an MV072 protein with unique complementarity-determining regions, i.e., a binding protein specifically binding to proprotein convertase subtilisin kexin type 9 (PCSK9). The protein can specifically bind to PCSK9, effectively inhibit the function of PCSK9 and reduce plasma LDL cholesterol level. Further provided is an application of the binding protein in treating diseases related to or influenced by the function of PCSK9.

12 Claims, 4 Drawing Sheets
Specification includes a Sequence Listing.

9M283           9M284

Human PCSK9

Monkey PCSK9

Mouse PCSK9

SEQUENCE LISTING

<160> NUMBER OF SEQ ID NOS: 32

<210> SEQ ID NO 1
<211> LENGTH: 1419
<212> TYPE: DNA
<213> ORGANISM: Homo Sapiens

<400> SEQUENCE: 1

```
atggacccca agggcagcct gagctggaga atcctgctgt tcctgagcct ggccttcgag      60
ctgagctacg ccaggtgca gctggtgcag tctggtgccg aagtgaagaa acccggctcc     120
tccgtgaagg tgtcctgcaa ggcctccgcc ttcaccttcg acagcttcgg catgcactgg     180
gtgcgacagg cccctggaca gggcctggaa tggatgggcc tgctttggag cgacggctcc     240
ggcgagtact acgccgactc cgctaagggc cggttcacca tctcccggga caactccaag     300
aacaccctgt acctgcagat gaactccctg cggagcgacg acaccgccgt gtactactgt     360
gccagagcga tgggcgccat ctactactac tacgccatgg acgtgtgggg ccagggcacc     420
acagtgaccg tgtcatctgc tagcaccaag ggcccatcgg tcttccccct ggcgccctgc     480
tccaggagca cctccgagag cacagcggcc ctgggctgcc tggtcaagga ctacttcccc     540
gaaccggtga cggtgtcgtg gaactcaggc gctctgacca gcggcgtgca caccttcccg     600
gctgtcctac agtcctcagg actctactcc ctcagcagcg tggtgaccgt gccctccagc     660
aacttcggca cccagaccta cacctgcaac gtagatcaca agcccagcaa caccaaggtg     720
gacaagacag ttgagcgcaa atgttgtgtc gagtgcccac cgtgcccagc accacctgtg     780
gcaggaccgt cagtcttcct cttccccca aaacccaagg acaccctcat gatctcccgg     840 accccctgagg tcacgtgcgt ggtggtggac gtgagccacg aagacccga ggtccagttc     900 aactggtacg tggacggcgt ggaggtgcat aatgccaaga caaagccacg ggaggagcag     960
ttcaacagca cgttccgtgt ggtcagcgtc ctcaccgttg tgcaccagga ctggctgaac    1020
ggcaaggagt acaagtgcaa ggtctccaac aaaggcctcc cagcccccat cgagaaaacc    1080
atctccaaaa ccaaagggca gccccgagaa ccacaggtgt acaccctgcc cccatcccgg    1140
gaggagatga ccaagaacca ggtcagcctg acctgcctgg tcaaaggctt ctaccccagc    1200
gacatcgccg tggagtggga gagcaatggg cagccggaga caactacaa gaccacacct    1260 cccatgctgg actccgacgg ctccttcttc ctctacagca agctcaccgt ggacaagagc    1320
```

```
aggtggcagc aggggaacgt cttctcatgc tccgtgatgc atgaggctct gcacaaccac    1380
tacacgcaga agagcctctc cctgtctccg ggttagtaa                           1419
```

<210> SEQ ID NO 2
<211> LENGTH: 471
<212> TYPE: PRT
<213> ORGANISM: Homo Sapiens

<400> SEQUENCE: 2

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ser Ser Val Lys Val Ser Cys Lys Ala
        35                  40                  45

Ser Ala Phe Thr Phe Asp Ser Phe Gly Met His Trp Val Arg Gln Ala
    50                  55                  60

Pro Gly Gln Gly Leu Glu Trp Met Gly Leu Leu Trp Ser Asp Gly Ser
65                  70                  75                  80

Gly Glu Tyr Tyr Ala Asp Ser Ala Lys Gly Arg Phe Thr Ile Ser Arg
                85                  90                  95

Asp Asn Ser Lys Asn Thr Leu Tyr Leu Gln Met Asn Ser Leu Arg Ser
            100                 105                 110

Asp Asp Thr Ala Val Tyr Tyr Cys Ala Arg Ala Met Gly Ala Ile Tyr
        115                 120                 125

Tyr Tyr Tyr Ala Met Asp Val Trp Gly Gln Gly Thr Thr Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
            340                 345                 350
```

```
Leu Pro Ala Pro Ile Glu Lys Thr Ile Ser Lys Thr Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly
465                 470

<210> SEQ ID NO 3
<211> LENGTH: 714
<212> TYPE: DNA
<213> ORGANISM: Homo Sapiens

<400> SEQUENCE: 3
atgtccgtgc ctacccaggt gctgggactg ctgctgctgt ggctgaccga cgccagatgt      60
cagtctgctc tgacccagcc tccttccgtg tctggctctc ctggccagtc cgtgaccatc     120
tcctgcaccg gcacctcctc aacatcggc aaccaattcg tgtcctggta tcagcagctg     180
cccggcaccg ctcccaaact gatgatctac gagtacaaca agcggccctc cggcgtgccc     240
gaccggttct ctggatctaa gtccggcaac accgcctccc tgaccatcag cggactgcag     300
acaggcgacg aggccgacta ctactgcggc tcctgggact cttccctgtc cggctatgtg     360
ttcggcaccg gcaccagagt gaccgtgctg gacagccta aggccgctcc ttccgtgacc     420
ctgttccctc catcctccga ggaactgcag gccaacaagg ccaccctcgt gtgcctgatc     480
tccgacttct accctggcgc cgtgaccgtg gcctggaagg ctgatagctc tcctgtgaag     540
gccggcgtgg aaaccaccac cccttccaag cagtccaaca caaatacgc cgcctcctcc     600 tacctgtccc tgacccctga gcagtggaag tcccaccggt cctacagctg ccaagtgacc     660
cacgagggct ccaccgtgga aaagaccgtg gctcctaccg agtgctcctg ataa           714

<210> SEQ ID NO 4
<211> LENGTH: 236
<212> TYPE: PRT
<213> ORGANISM: Homo Sapiens

<400> SEQUENCE: 4

Met Ser Val Pro Thr Gln Val Leu Gly Leu Leu Leu Leu Trp Leu Thr
1               5                   10                  15

Asp Ala Arg Cys Gln Ser Ala Leu Thr Gln Pro Pro Ser Val Ser Gly
            20                  25                  30

Ser Pro Gly Gln Ser Val Thr Ile Ser Cys Thr Gly Thr Ser Ser Asn
        35                  40                  45

Ile Gly Asn Gln Phe Val Ser Trp Tyr Gln Gln Leu Pro Gly Thr Ala
    50                  55                  60

Pro Lys Leu Met Ile Tyr Glu Tyr Asn Lys Arg Pro Ser Gly Val Pro
65                  70                  75                  80
```

Asp Arg Phe Ser Gly Ser Lys Ser Gly Asn Thr Ala Ser Leu Thr Ile
            85                  90                  95
Ser Gly Leu Gln Thr Gly Asp Glu Ala Asp Tyr Tyr Cys Gly Ser Trp
        100                 105                 110
Asp Ser Ser Leu Ser Gly Tyr Val Phe Gly Thr Gly Thr Arg Val Thr
        115                 120                 125
Val Leu Gly Gln Pro Lys Ala Ala Pro Ser Val Thr Leu Phe Pro Pro
130                 135                 140
Ser Ser Glu Glu Leu Gln Ala Asn Lys Ala Thr Leu Val Cys Leu Ile
145                 150                 155                 160
Ser Asp Phe Tyr Pro Gly Ala Val Thr Val Ala Trp Lys Ala Asp Ser
            165                 170                 175
Ser Pro Val Lys Ala Gly Val Glu Thr Thr Thr Pro Ser Lys Gln Ser
        180                 185                 190
Asn Asn Lys Tyr Ala Ala Ser Ser Tyr Leu Ser Leu Thr Pro Glu Gln
        195                 200                 205
Trp Lys Ser His Arg Ser Tyr Ser Cys Gln Val Thr His Glu Gly Ser
        210                 215                 220
Thr Val Glu Lys Thr Val Ala Pro Thr Glu Cys Ser
225                 230                 235

<210> SEQ ID NO 5
<211> LENGTH: 1419
<212> TYPE: DNA
<213> ORGANISM: Homo Sapiens

<400> SEQUENCE: 5
atggacccca agggcagcct gagctggaga atcctgctgt tcctgagcct ggccttcgag    60
ctgagctacg gccaggtgca gctggtgcag tctggtgccg aagtgaagaa acccggctcc   120
tccgtgaagg tgtcctgcaa ggcctccgcc ttcaccttcg acagcttcgg catgcactgg   180
gtgcgacagg ccctgggaca gggcctggaa tggatgggcc tgctttggag cgacggctcc   240
gacgagtact acgccgactc cgctaagggc cggttcacca tctcccggga caactccaag   300
aacaccctgt acctgcagat gaactccctg cggagcgacg acaccgccgt gtactactgt   360
gccagagcgt tgggcgcgat ctacagctac tacgccatgg acgtgtgggg ccagggcacc   420
acagtgaccg tgtcatctgc tagcaccaag ggcccatcgg tcttcccect ggcgccctgc   480
tccaggagca cctccgagag cacagcggcc ctgggctgcc tggtcaagga ctacttcccc   540
gaaccggtga cggtgtcgtg gaactcaggc gctctgacca gcggcgtgca caccttcccg   600
gctgtcctac agtcctcagg actctactcc ctcagcagcg tggtgaccgt gccctccagc   660
aacttcggca cccagaccta cacctgcaac gtagatcaca agcccagcaa caccaaggtg   720
gacaagacag ttgagcgcaa atgttgtgtc gagtgcccac cgtgcccagc accacctgtg   780
gcaggaccgt cagtcttcct cttcccccca aaacccaagg acaccctcat gatctcccgg   840
acccctgagg tcacgtgcgt ggtggtggac gtgagccacg aagaccccga ggtccagttc   900
aactggtacg tggacggcgt ggaggtgcat aatgccaaga caaagccacg ggaggagcag   960
ttcaacagca cgttccgtgt ggtcagcgtc ctcaccgttg tgcaccagga ctggctgaac  1020
ggcaaggagt acaagtgcaa ggtctccaac aaaggcctcc cagcccccat cgagaaaacc  1080
atctccaaaa ccaaagggca gccccgagaa ccacaggtgt acaccctgcc cccatcccgg  1140
gaggagatga ccaagaacca ggtcagcctg acctgcctgg tcaaaggctt ctaccccagc  1200
gacatcgccg tggagtggga gagcaatggg cagccggaga acaactacaa gaccacacct  1260

```
cccatgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggttagtaa                           1419
```

<210> SEQ ID NO 6
<211> LENGTH: 471
<212> TYPE: PRT
<213> ORGANISM: Homo Sapiens

<400> SEQUENCE: 6

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ser Val Lys Val Ser Cys Lys Ala
        35                  40                  45

Ser Ala Phe Thr Phe Asp Ser Phe Gly Met His Trp Val Arg Gln Ala
    50                  55                  60

Pro Gly Gln Gly Leu Glu Trp Met Gly Leu Leu Trp Ser Asp Gly Ser
65                  70                  75                  80

Asp Glu Tyr Tyr Ala Asp Ser Ala Lys Gly Arg Phe Thr Ile Ser Arg
                85                  90                  95

Asp Asn Ser Lys Asn Thr Leu Tyr Leu Gln Met Asn Ser Leu Arg Ser
            100                 105                 110

Asp Asp Thr Ala Val Tyr Tyr Cys Ala Arg Ala Leu Gly Ala Ile Tyr
        115                 120                 125

Ser Tyr Tyr Ala Met Asp Val Trp Gly Gln Gly Thr Thr Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
```

-continued

```
                     340                 345                 350
Leu Pro Ala Pro Ile Glu Lys Thr Ile Ser Lys Thr Lys Gly Gln Pro
                355                 360                 365
Arg Glu Pro Gln Val Tyr Thr Leu Pro Pro Ser Arg Glu Glu Met Thr
            370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Met Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly
465                 470

<210> SEQ ID NO 7
<211> LENGTH: 10
<212> TYPE: PRT
<213> ORGANISM: Homo Sapiens

<400> SEQUENCE: 7

Ala Phe Thr Phe Asp Ser Phe Gly Met His
1               5                   10

<210> SEQ ID NO 8
<211> LENGTH: 17
<212> TYPE: PRT
<213> ORGANISM: Homo Sapiens

<400> SEQUENCE: 8

Leu Leu Trp Ser Asp Gly Ser Gly Glu Tyr Tyr Ala Asp Ser Ala Lys
1               5                   10                  15
Gly

<210> SEQ ID NO 9
<211> LENGTH: 13
<212> TYPE: PRT
<213> ORGANISM: Homo Sapiens

<400> SEQUENCE: 9

Ala Met Gly Ala Ile Tyr Tyr Tyr Tyr Ala Met Asp Val
1               5                   10

<210> SEQ ID NO 10
<211> LENGTH: 13
<212> TYPE: PRT
<213> ORGANISM: Homo Sapiens

<400> SEQUENCE: 10

Thr Gly Thr Ser Ser Asn Ile Gly Asn Gln Phe Val Ser
1               5                   10

<210> SEQ ID NO 11
<211> LENGTH: 7
<212> TYPE: PRT
<213> ORGANISM: Homo Sapiens

<400> SEQUENCE: 11
```

Glu Tyr Asn Lys Arg Pro Ser
1               5

<210> SEQ ID NO 12
<211> LENGTH: 11
<212> TYPE: PRT
<213> ORGANISM: Homo Sapiens

<400> SEQUENCE: 12

Gly Ser Trp Asp Ser Ser Leu Ser Gly Tyr Val
1               5                   10

<210> SEQ ID NO 13
<211> LENGTH: 17
<212> TYPE: PRT
<213> ORGANISM: Homo Sapiens

<400> SEQUENCE: 13

Leu Leu Trp Ser Asp Gly Ser Asp Glu Tyr Tyr Ala Asp Ser Ala Lys
1               5                   10                  15

Gly

<210> SEQ ID NO 14
<211> LENGTH: 13
<212> TYPE: PRT
<213> ORGANISM: Homo Sapiens

<400> SEQUENCE: 14

Ala Leu Gly Ala Ile Tyr Ser Tyr Tyr Ala Met Asp Val
1               5                   10

<210> SEQ ID NO 15
<211> LENGTH: 30
<212> TYPE: DNA
<213> ORGANISM: Homo Sapiens

<400> SEQUENCE: 15
gccttcacct tcgacagctt cggcatgcac                                  30

<210> SEQ ID NO 16
<211> LENGTH: 51
<212> TYPE: DNA
<213> ORGANISM: Homo Sapiens

<400> SEQUENCE: 16
ctgctttgga gcgacggctc cggcgagtac tacgccgact ccgctaaggg c          51

<210> SEQ ID NO 17
<211> LENGTH: 39
<212> TYPE: DNA
<213> ORGANISM: Homo Sapiens

<400> SEQUENCE: 17
gcgatgggcg ccatctacta ctactacgcc atggacgtg                        39

<210> SEQ ID NO 18
<211> LENGTH: 39
<212> TYPE: DNA
<213> ORGANISM: Homo Sapiens

<400> SEQUENCE: 18
accggcacct cctccaacat cggcaaccaa ttcgtgtcc                        39

<210> SEQ ID NO 19
<211> LENGTH: 21
<212> TYPE: DNA
<213> ORGANISM: Homo Sapiens

<400> SEQUENCE: 19
gagtacaaca agcggccctc c                                              21

<210> SEQ ID NO 20
<211> LENGTH: 33
<212> TYPE: DNA
<213> ORGANISM: Homo Sapiens

<400> SEQUENCE: 20
ggctcctggg actcttccct gtccggctat gtg                                 33

<210> SEQ ID NO 21
<211> LENGTH: 51
<212> TYPE: DNA
<213> ORGANISM: Homo Sapiens

<400> SEQUENCE: 21
ctgctttgga gcgacggctc cgacgagtac tacgccgact ccgctaaggg c              51

<210> SEQ ID NO 22
<211> LENGTH: 39
<212> TYPE: DNA
<213> ORGANISM: Homo Sapiens

<400> SEQUENCE: 22
gcgttgggcg cgatctacag ctactacgcc atggacgtg                           39

<210> SEQ ID NO 23
<211> LENGTH: 1347
<212> TYPE: DNA
<213> ORGANISM: Homo Sapiens

<400> SEQUENCE: 23
caggtgcagc tggtgcagtc tggtgccgaa gtgaagaaac ccggctcctc cgtgaaggtg      60
tcctgcaagg cctccgcctt caccttcgac agcttcggca tgcactgggt gcgacaggcc     120
cctggacagg gcctggaatg gatgggcctg ctttggagcg acggctccgg cgagtactac     180
gccgactccg ctaagggccg gttcaccatc tcccgggaca actccaagaa caccctgtac     240
ctgcagatga actccctgcg gagcgacgac accgccgtgt actactgtgc cagagcgatg     300
ggcgccatct actactacta cgccatggac gtgtggggcc agggcaccac agtgaccgtg     360
tcatctgcta gcaccaaggg cccatcggtc ttccccctgg cgccctgctc caggagcacc     420
tccgagagca cagcggccct gggctgcctg gtcaaggact acttccccga accggtgacg     480
gtgtcgtgga actcaggcgc tctgaccagc ggcgtgcaca ccttcccggc tgtcctacag     540
tcctcaggac tctactccct cagcagcgtg gtgaccgtgc cctccagcaa cttcggcacc     600
cagacctaca cctgcaacgt agatcacaag cccagcaaca ccaaggtgga caagacagtt     660
gagcgcaaat gttgtgtcga gtgcccaccg tgcccagcac cacctgtggc aggaccgtca     720
gtcttcctct tccccccaaa acccaaggac accctcatga tctcccggac ccctgaggtc     780
acgtgcgtgg tggtggacgt gagccacgaa gaccccgagg tccagttcaa ctggtacgtg     840
gacggcgtgg aggtgcataa tgccaagaca aagccacggg aggagcagtt caacagcacg     900
ttccgtgtgg tcagcgtcct caccgttgtg caccaggact ggctgaacgg caaggagtac     960

-continued

```
aagtgcaagg tctccaacaa aggcctccca gcccccatcg agaaaaccat ctccaaaacc    1020
aaagggcagc cccgagaacc acaggtgtac accctgcccc catcccggga ggagatgacc    1080
aagaaccagg tcagcctgac ctgcctggtc aaaggcttct accccagcga catcgccgtg    1140
gagtgggaga gcaatgggca gccggagaac aactacaaga ccacacctcc catgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg ttagtaa                                        1347
```

<210> SEQ ID NO 24
<211> LENGTH: 447
<212> TYPE: PRT
<213> ORGANISM: Homo Sapiens

<400> SEQUENCE: 24

```
Gln Val Gln Leu Val Gln Ser Gly Ala Glu Val Lys Lys Pro Gly Ser
1               5                   10                  15

Ser Val Lys Val Ser Cys Lys Ala Ser Ala Phe Thr Phe Asp Ser Phe
            20                  25                  30

Gly Met His Val Arg Gln Ala Pro Gly Gln Gly Leu Glu Trp Met
        35                  40                  45

Gly Leu Leu Trp Ser Asp Gly Ser Gly Glu Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Ala Met Gly Ala Ile Tyr Tyr Tyr Ala Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300
```

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 25
<211> LENGTH: 654
<212> TYPE: DNA
<213> ORGANISM: Homo Sapiens

<400> SEQUENCE: 25
cagtctgctc tgacccagcc tccttccgtg tctggctctc ctggccagtc cgtgaccatc      60
tcctgcaccg gcacctcctc caacatcggc aaccaattcg tgtcctggta tcagcagctg     120
cccggcaccg ctcccaaact gatgatctac gagtacaaca gcggccctc cggcgtgccc      180
gaccggttct ctggatctaa gtccggcaac accgcctccc tgaccatcag cggactgcag     240
acaggcgacg aggccgacta ctactgcggc tcctgggact cttccctgtc cggctatgtg     300
ttcggcaccg gcaccagagt gaccgtgctg ggacagccta aggccgctcc ttccgtgacc     360
ctgttccctc catcctccga ggaactgcag gccaacaagg ccaccctcgt gtgcctgatc     420
tccgacttct accctggcgc cgtgaccgtg gcctggaagg ctgatagctc tcctgtgaag     480
gccggcgtgg aaaccaccac cccttccaag cagtccaaca caaatacgc cgcctcctcc      540
tacctgtccc tgaccccga gcagtggaag tccaccggt cctacagctg ccaagtgacc       600
cacgagggct ccaccgtgga aaagaccgtg gctcctaccg agtgctcctg ataa            654

<210> SEQ ID NO 26
<211> LENGTH: 216
<212> TYPE: PRT
<213> ORGANISM: Homo Sapiens

<400> SEQUENCE: 26

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asn Ile Gly Asn Gln
            20                  25                  30

Phe Val Ser Trp Tyr Gln Gln Leu Pro Gly Thr Ala Pro Lys Leu Met
        35                  40                  45

Ile Tyr Glu Tyr Asn Lys Arg Pro Ser Gly Val Pro Asp Arg Phe Ser
    50                  55                  60

Gly Ser Lys Ser Gly Asn Thr Ala Ser Leu Thr Ile Ser Gly Leu Gln

```
            65                  70                  75                  80
Thr Gly Asp Glu Ala Asp Tyr Tyr Cys Gly Ser Trp Asp Ser Ser Leu
                85                  90                  95

Ser Gly Tyr Val Phe Gly Thr Gly Thr Arg Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 27
<211> LENGTH: 1347
<212> TYPE: DNA
<213> ORGANISM: Homo Sapiens

<400> SEQUENCE: 27

```
caggtgcagc tggtgcagtc tggtgccgaa gtgaagaaac ccggctcctc cgtgaaggtg      60
tcctgcaagg cctccgcctt caccttcgac agcttcggca tgcactgggt gcgacaggcc     120
cctggacagg gcctggaatg gatgggcctg ctttggagcg acggctccga cgagtactac     180
gccgactccg ctaagggccg gttcaccatc tcccgggaca actccaagaa caccctgtac     240
ctgcagatga actccctgcg gagcgacgac accgccgtgt actactgtgc cagagcgttg     300
ggcgcgatct acagctacta cgccatggac gtgtggggcc agggcaccac agtgaccgtg     360
tcatctgcta gcaccaaggg cccatcggtc ttccccctgg cgccctgctc caggagcacc     420
tccgagagca gcgcggccct gggctgcctg gtcaaggact acttccccga accggtgacg     480
gtgtcgtgga actcaggcgc tctgaccagc ggcgtgcaca ccttcccggc tgtcctacag     540
tcctcaggac tctactccct cagcagcgtg gtgaccgtgc cctccagcaa cttcggcacc     600
cagacctaca cctgcaacgt agatcacaag cccagcaaca ccaaggtgga caagacagtt     660
gagcgcaaat gttgtgtcga gtgcccaccg tgcccagcac cacctgtggc aggaccgtca     720
gtcttcctct tccccccaaa acccaaggac accctcatga tctcccggac ccctgaggtc     780
acgtgcgtgg tggtggacgt gagccacgaa gaccccgagg tccagttcaa ctggtacgtg     840
gacggcgtgg aggtgcataa tgccaagaca aagccacggg aggagcagtt caacagcacg     900
ttccgtgtgg tcagcgtcct caccgttgtg caccaggact ggctgaacgg caaggagtac     960
aagtgcaagg tctccaacaa aggcctccca gcccccatcg agaaaaccat ctccaaaacc    1020
aaagggcagc cccgagaacc acaggtgtac accctgcccc catcccggga ggagatgacc    1080
aagaaccagg tcagcctgac ctgcctggtc aaaggcttct accccagcga catcgccgtg    1140
gagtgggaga gcaatgggca gccggagaac aactacaaga ccacacctcc catgctggac    1200
tccgacggct ccttcttcct ctacagcaag ctcaccgtgg acaagagcag gtggcagcag    1260
```

```
gggaacgtct tctcatgctc cgtgatgcat gaggctctgc acaaccacta cacgcagaag    1320
agcctctccc tgtctccggg ttagtaa                                        1347
```

<210> SEQ ID NO 28
<211> LENGTH: 447
<212> TYPE: PRT
<213> ORGANISM: Homo Sapiens

<400> SEQUENCE: 28

```
Gln Val Gln Leu Val Gln Ser Gly Ala Glu Val Lys Lys Pro Gly Ser
1               5                   10                  15

Ser Val Lys Val Ser Cys Lys Ala Ser Ala Phe Thr Phe Asp Ser Phe
            20                  25                  30

Gly Met His Trp Val Arg Gln Ala Pro Gly Gln Gly Leu Glu Trp Met
        35                  40                  45

Gly Leu Leu Trp Ser Asp Gly Ser Asp Glu Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Ala Leu Gly Ala Ile Tyr Ser Tyr Tyr Ala Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

355                 360                 365
Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 29
<211> LENGTH: 1356
<212> TYPE: DNA
<213> ORGANISM: Artifical sequence
<220> FEATURE:
<221> NAME/KEY: misc_feature
<223> OTHER INFORMATION: 9M284QL

<400> SEQUENCE: 29
caggtgcagc tggtgcagtc tggtgccgaa gtgaagaaac ccggctcctc cgtgaaggtg       60
tcctgcaagg cctccgcctt caccttcgac agcttcggca tgcactgggt gcgacaggcc      120
cctggacagg gcctggaatg gatgggcctg ctttggagcg acggctccgg cgagtactac      180
gccgactccg ctaagggccg gttcaccatc tcccgggaca ctccaagaa caccctgtac       240 ctgcagatga actccctgcg gagcgacgac accgccgtgt actactgtgc cagagcgatg      300
ggcgccatct actactacta cgccatggac gtgtggggcc agggcaccac agtgaccgtg      360
tcatctgcta gcaccaaggg cccatcggtc ttccccctgg cacctcctc caagagcacc       420 tctgggggca gcggccct gggctgcctg gtcaaggact acttccccga accggtgacg      480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga caagaaagtt      660
gagcccaaat cttgtgacaa aactcacaca tgcccaccgt gcccagcacc tgaactcctg      720
gggggaccgt cagtcttcct cttccccca aaacccaagg accagctcat gatctcccgg      780
acccctgagg tcacatgcgt ggtggtggac gtgagccacg aagaccctga ggtcaagttc      840
aactggtacg tggacggcgt ggaggtgcat aatgccaaga caaagccgcg ggaggagcag      900
tacaacagca cgtaccgggt ggtcagcgtc ctcaccgtcc tgcaccagga ctggctgaat      960
ggcaaggagt acaagtgcaa ggtctccaac aaagccctcc cagcccccat cgagaaaacc     1020
atctccaaag ccaaagggca gccccgagaa ccacaggtgt acaccctgcc cccatcccgg     1080
gatgagctga ccaagaacca ggtcagcctg acctgcctgg tcaaaggctt ctatcccagc     1140
gacatcgccg tggagtggga gagcaatggg cagccggaga caactacaa gaccacgcct      1200 cccgtgctgg actccgacgg ctccttcttc ctctacagca agctcaccgt ggacaagagc     1260
aggtggcagc aggggaacgt cttctcatgc tccgtgttgc atgaggctct gcacaaccac     1320
tacacgcaga agagcctctc cctgtctccg ggttag                               1356

<210> SEQ ID NO 30
<211> LENGTH: 451
<212> TYPE: PRT
<213> ORGANISM: Artifical sequence

```
<220> FEATURE:
<221> NAME/KEY: MISC_FEATURE
<223> OTHER INFORMATION: 9M284QL

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Ala Phe Thr Phe Asp Ser Phe
            20                  25                  30

Gly Met His Trp Val Arg Gln Ala Pro Gly Gln Gly Leu Glu Trp Met
        35                  40                  45

Gly Leu Leu Trp Ser Asp Gly Ser Gly Glu Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Ala Met Gly Ala Ile Tyr Tyr Tyr Ala Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Gln Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

Pro Val Leu Asp Ser Asp Gly Ser Phe Phe Leu Tyr Ser Lys Leu Thr
        385             390             395             400
                405                     410                     415

Val Asp Lys Ser Arg Trp Gln Gln Gly Asn Val Phe Ser Cys Ser Val
                420                     425                     430

Leu His Glu Ala Leu His Asn His Tyr Thr Gln Lys Ser Leu Ser Leu
        435                     440                     445

Ser Pro Gly
    450

<210> SEQ ID NO 31
<211> LENGTH: 1356
<212> TYPE: DNA
<213> ORGANISM: Artifical sequence
<220> FEATURE:
<221> NAME/KEY: misc_feature
<223> OTHER INFORMATION: 9M284YTE

<400> SEQUENCE: 31
caggtgcagc tggtgcagtc tggtgccgaa gtgaagaaac ccggctcctc cgtgaaggtg      60
tcctgcaagg cctccgcctt caccttcgac agcttcggca tgcactgggt gcgacaggcc     120
cctggacagg gcctggaatg gatgggcctg cttggagcg acggctccgg cgagtactac      180
gccgactccg ctaagggccg gttcaccatc tcccgggaca actccaagaa cacccctgtac    240 ctgcagatga actccctgcg gagcgacgac accgccgtgt actactgtgc cagagcgatg    300
ggcgccatct actactacta cgccatggac gtgtggggcc agggcaccac agtgaccgtg    360
tcatctgcta gcaccaaggg cccatcggtc ttccccctgg cacccctcc caagagcacc    420 tctggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaactcctg    720
gggggaccgt cagtcttcct cttcccccca aaacccaagg acaccctcta tcacccgg      780 gaacctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgggt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga caactacaa gaccacgcct    1200 cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggttga                              1356

<210> SEQ ID NO 32
<211> LENGTH: 451
<212> TYPE: PRT
<213> ORGANISM: Artifical sequence
<220> FEATURE:
<221> NAME/KEY: MISC_FEATURE
<223> OTHER INFORMATION: 9M284YTE

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Ala Phe Thr Phe Asp Ser Phe
            20                  25                  30

Gly Met His Trp Val Arg Gln Ala Pro Gly Gln Gly Leu Glu Trp Met
        35                  40                  45

Gly Leu Leu Trp Ser Asp Gly Ser Gly Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Ala Met Gly Ala Ile Tyr Tyr Tyr Ala Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Tyr Ile Thr Arg Glu Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr

-continued

```
                405                 410                 415
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450
```

LONG-ACTING PCSK9-SPECIFIC BINDING PROTEIN AND APPLICATION THEREOF

CROSS-REFERENCE TO RELATED APPLICATIONS

This application is a U.S. National Phase filing under 35 U.S.C. § 371 of PCT Application Serial No. PCT/CN2017/087536 filed on Jun. 8, 2017, which claims priority to Chinese Patent Application Serial No. 201610405036.7 filed on Jun. 8, 2016; the contents of each of the respective applications are incorporated herein by reference in their entireties.

FIELD OF THE INVENTION

The invention belongs to the field of immunology, and more particularly, the invention relates to proprotein convertase subtilisin kexin type 9 (PCSK9)-specific binding protein and application thereof.

BACKGROUND OF THE INVENTION

Cardiovascular disease is the leading cause of human death. Low-density lipoprotein cholesterol (LDL-C) has been demonstrated to be one of the major causes of cardiovascular disease. This effect of LDL-C is relatively independent and can be effectively controlled. Over the past 20 years, use of statins as lipid-lowering drugs has successfully reduced the incidence of cardiovascular disease.

However, treatment with statins does not always work, and there are still needs for other hypolipidemic therapies. Some patients, especially those with familial hypercholesterolaemia (FH), are often insensitive to statins. Even with the highest dosage of statins, it is difficult for these patients to achieve a lower LDL-C level. In addition, statins have some side effects such as muscle pain and rhabdomyolysis, which may cause some patients to be unable to use statins or only be treated with a small dosage of statins to control blood lipid levels. Proprotein convertase subtilisin kexin type 9 (PCSK9) inhibitor is such a new type of drug that provides a new option for controlling the concentration of LDL-C in blood.

PCSK9 is a serine protease involved in the regulation of the level of low-density lipoprotein receptor (LDLR). In-vitro experiments have confirmed that the level of LDLR on the cell surface decreases after adding PCSK9 to HepG2 cells. Experiments in mice have shown that increased levels of PCSK9 protein can reduce the protein level of LDLR in the liver, while the LDLR levels are elevated in PCSK9 knockout mice relative to normal mice. It has been shown that PCSK9 directly binds to LDLR and is phagocytosed along with LDLR, and co-immunofluorescence of PCSK9 and LDLR occurs throughout the endocytic pathway. Currently, there is no direct evidence to prove that PCSK9 degrades extracellular LDLR, and the mechanism by which it reduces extracellular LDLR protein levels remains unclear.

Studies have confirmed that PCSK9 plays a role in regulating LDL production. The expression or up-regulation of PCSK9 is related to increased plasma levels of LDL cholesterol, while the inhibition or lack of PCSK9 expression is related to low plasma levels of LDL cholesterol.

Therefore, it is important to prepare a therapeutic-based PCSK9 antagonist, particularly a monoclonal antibody that specifically binds to PCSK9, which inhibits or antagonizes PCSK9 activity and corresponding effects of PCSK9 under various therapeutic conditions. PCSK9 inhibitors under investigation may include small interfering RNA (siRNA), antisense oligonucleotides (ASOs), monoclonal antibodies, and some specific binding fusion proteins produced by new techniques, such as Fusion protein produced by adnectin technology. Currently, PCSK9 inhibitors under investigation are mainly as follows: siRNA drug, RG7652 (Alnylam Pharmaceuticals/The Medicines Company); fusion protein produced by Adnectin technology, BMS-962476 (BMS); ASO drug, ALN-PCS02 (Idera Pharmaceuticals); and antibody drugs, such as Bococizumab (Pfizer/Rinat), LGT-209 (Novartis), and the like.

However, it has been found in animal experiments or clinical studies that some PCSK9 monoclonal antibody inhibitors have insufficient specificity, affinity, or side effect concerns. There is, therefore, a need to further optimize and prepare novel anti-PCSK9 antibodies in the art.

SUMMARY OF THE INVENTION

An objective of the invention is to provide a novel PCSK9-specific binding protein, MV072 and uses thereof.

In the first aspect of the invention, binding protein MV072 that specifically binds to PCSK9 is provided, said binding protein has a light chain variable region and a heavy chain variable region, and the amino acid sequence of the heavy chain variable region CDR1 thereof is set forth in SEQ ID NO: 7;

the amino acid sequence of the heavy chain variable region CDR2 thereof is set forth in SEQ ID NO: 8 or SEQ ID NO: 13;

the amino acid sequence of the heavy chain variable region CDR3 thereof is set forth in SEQ ID NO: 9 or SEQ ID NO: 14;

the amino acid sequence of the light chain variable region CDR1 thereof is set forth in SEQ ID NO: 10;

the amino acid sequence of the light chain variable region CDR2 thereof is set forth in SEQ ID NO:11; and the amino acid sequence of its light chain variable region CDR3 is set forth in SEQ ID NO: 12.

In a preferred embodiment of the invention, the binding protein MV072 that specifically binds to PCSK9 is selected from the group consisting of:

(a) a binding protein in which the amino acid sequences of CDR1, CDR2 and CDR3 in the heavy chain variable region are set forth in SEQ ID NO: 7, SEQ ID NO: 8, and SEQ ID NO: 9, respectively; and the amino acid sequences of CDR1, CDR2 and CDR3 in the light chain variable region are set forth in SEQ ID NO: 10, SEQ ID NO: 11, and SEQ ID NO: 12, respectively; or (b) a binding protein in which the amino acid sequences of CDR1, CDR2 and CDR3 in the heavy chain variable region are set forth in SEQ ID NO: 7, SEQ ID NO: 13, and SEQ ID NO: 14, respectively; and, the amino acid sequences of CDR1, CDR2, and CDR3 in the light chain variable region are set forth in SEQ ID NO: 10, SEQ ID NO: 11, and SEQ ID NO: 12, respectively.

In another preferred embodiment, the binding protein MV072 that specifically binds to PCSK9 is characterized in that the amino acid sequence of the heavy chain variable region thereof is set forth in SEQ ID NO: 2 or SEQ ID NO: 24, and the amino acid sequence of the light chain thereof is set forth in SEQ ID NO: 4 or SEQ ID NO: 26; or the amino acid sequence of the heavy chain variable region thereof is set forth in SEQ ID NO: 6 or SEQ ID NO: 28, and the amino acid sequence of the light chain variable region thereof is set forth in SEQ ID NO: 4 or SEQ ID NO: 26.

In another preferred embodiment, in the binding protein MV072 that specifically binds to PCSK9, the variable region of the heavy chain thereof is further linked to IgG1 Fc.

In another preferred embodiment, the IgG1 Fc is a mutant IgG1 Fc carrying QL mutations (corresponding to the fusion sequence of SEQ ID NO: 30, with corresponding mutations of T255Q/M433L) or YTE mutations (corresponding to the fusion sequence of SEQ ID NO: 32, with corresponding mutations of M257Y/S259T/T261E).

In another preferred embodiment, the amino acid sequence obtained after ligation of the heavy chain variable region to an IgG1 Fc is set forth in SEQ ID NO: 30 or SEQ ID NO: 32.

In another preferred embodiment, the binding protein MV072 is an Fab, an F(ab'), an F(ab')2, an Fv, a dAb, an Fd, a complementarity determining region (CDR) fragment, a single chain antibody (scFv), a bivalent single-chain antibody, a single-stranded phage antibody, a bispecific di-chain antibody, a tribody, and a tetrabody.

In another preferred embodiment, the binding protein MV072 is a monoclonal antibody.

In another preferred embodiment, the heavy chain variable region and the light chain variable region of the binding protein MV072 have the amino acid sequences set forth in SEQ ID NO: 2 and SEQ ID NO: 4, respectively, or have the amino acid sequences set forth in SEQ ID NO: 6 and SEQ ID NO: 4, respectively, wherein the heavy chain constant region is selected from the constant regions of the heavy chain types IgG1, IgG2a, IgG2b, and IgG3, and the light chain constant region is the constant region of a kappa chain or a lambda chain.

In another aspect of the invention, a nucleic acid encoding the binding protein MV072 that specifically binds to PCSK9 is provided.

In another aspect of the invention, an expression vector comprising the nucleic acid is provided.

In another aspect of the invention, a host cell comprising said expression vector or said nucleic acid integrated in its genome is provided.

In another aspect of the invention, a use of the binding protein MV072 that specifically binds to PCSK9 in the preparation of a medicament for the diagnosis, treatment and/or prevention of PCSK9 expression or activity disorders-related diseases is provided.

In a preferred embodiment, the PCSK9 expression or activity disorders-related diseases include, but are not limited to: high serum cholesterol level-related disorders; preferably, including: hypercholesterolemia, coronary heart disease, metabolic syndrome and acute coronary syndrome.

In another aspect of the invention, a pharmaceutical composition comprising an effective amount of said binding protein MV072 that specifically binds to PCSK9 and a pharmaceutically acceptable carrier is provided.

In another aspect of the invention, a kit for treating and/or preventing PCSK9 expression or activity disorders-related diseases is provided, wherein said kit comprises said binding protein MV072 that specifically binds to PCSK9, or said pharmaceutical composition.

In another aspect of the invention, an immunoconjugate is provided, wherein the immunoconjugate comprises said binding protein MV072 that specifically binds to PCSK9, and a detectable label; preferably, said detection label includes a fluorescent label or a chromogenic label.

In another aspect of the invention, a detection kit for detecting the level of PCSK9 is provided, wherein the detection kit comprises said binding protein MV072 that specifically binds to PCSK9, or said immunoconjugate.

Other aspects of the invention will be apparent to those skilled in the art from this disclosure.

DETAILED DESCRIPTION OF THE INVENTION

Figure 1:
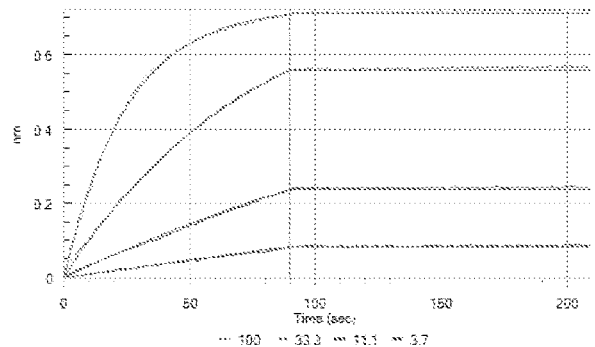
FIG. 1. Kinetic analysis results of the MV072 binding proteins (i.e., monoclonal antibodies 9M283 and 9M284) to human PCSK9 antigen, mouse PCSK9 antigen and *Macaca fascicularis* PCSK9 antigen, respectively.
Figure 1:
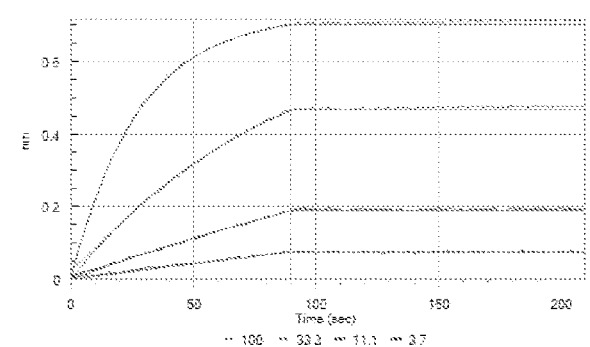
Figure 1:
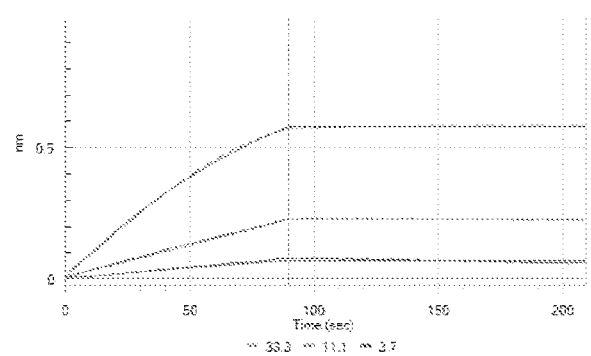
Figure 1:
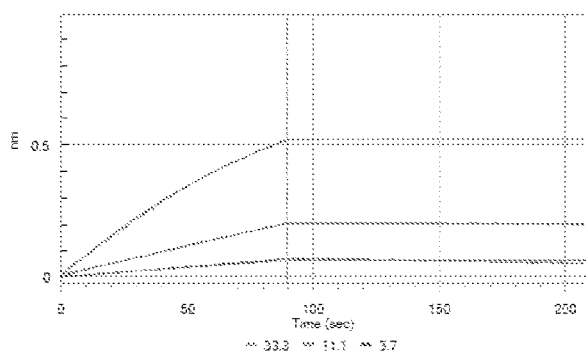
Figure 1:
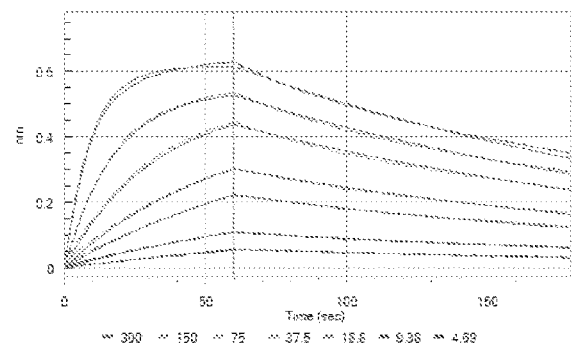
Figure 1:
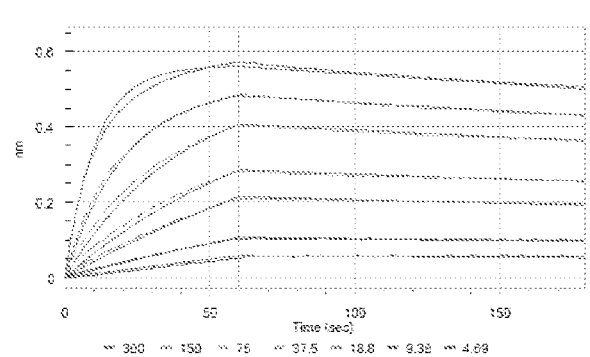

The inventors have conducted extensive and intensive researches to obtain binding protein MV072 that specifically binds to pre-protein convertase subtilisin kexin type 9 (PCSK9) and has unique complementarity determining regions (CDR regions), which specifically binds to PCSK9, effectively inhibits the function of PCSK9 and lowers plasma LDL cholesterol levels, and thus can be used to treat diseases related to or influenced by PCSK9 function.

Binding Protein MV072

The invention provides a PCSK9-specific binding protein MV072. The binding protein MV072 of the invention can be an intact immunoglobulin molecule or an antigen-binding fragment, including but not limited to an Fab fragment, an Fd fragment, an Fv fragment, an F(ab')2 fragment, a complementarity determining region (CDR) fragment, a single-chain antibody (scFv), a domain antibody, a bivalent single-chain antibody, a single-stranded phage antibody, a bispecific di-chain antibody, tribody, tetrabody, and the like.

CDR regions are protein sequences of immunological interest. In an embodiment of the invention, the binding protein may comprise two, three, four, five or all six CDR regions disclosed herein. Preferably, the binding protein MV072 of the invention comprises at least two CDRs disclosed herein.

Another aspect of the invention includes functional variants of the binding protein MV072 described herein. A variant molecule is considered to be a functional variant of the binding protein of the invention if it is capable of competing with the parental binding protein for specifically binding to PCSK9. In other words, the functional variant is still capable of binding to PCSK9 or a fragment thereof. Functional variants include, but are not limited to, those having substantially similar primary structural sequences but containing, for example, in vitro or in vivo chemically and/or biochemically modified derivatives that are not found in the parental binding protein. Such modifications include acetylation, acylation, covalent attachment of nucleotide or nucleotide derivatives, covalent attachment of lipids or lipid derivatives, cross-linking, disulfide bond formation, glycosylation, hydroxylation, methylation, oxidation, PEGylation, proteolytic processing, phosphorylation, and the like. In other words, the modification(s) in the amino acid and/or nucleotide sequence of the parent binding protein do not significantly affect or alter the binding properties of the binding protein encoded by the nucleotide sequence or containing the amino acid sequence, i.e., the binding protein still recognizes and binds to its target site.

The functional variants may have conservative sequence modifications, including nucleotide and amino acid substitutions, additions and deletions. These modifications can be introduced by well known standard techniques in the art, such as site-directed mutagenesis and random PCR-mediated mutagenesis, and can include natural and non-natural nucleotides and amino acids.

Conservative amino acid substitutions include substitutions in which an amino acid residue is replaced with another amino acid residue having similar structure or chemical property. Families of amino acid residues having similar side chains have been defined in the art. These families include amino acids with basic side chains (e.g., lysine, arginine, histidine), acidic side chain (e.g., aspartic acid, glutamic acid), uncharged polar side chain (e.g., asparagine, glutamine, serine, threonine, tyrosine, cysteine, tryptophan), non-polar side chain (e.g., glycine, alanine, valine, leucine, isoleucine, proline, phenylalanine, methionine), branched side chain (e.g., threonine, valine, isoleucine) and aromatic side chain (e.g., tyrosine, phenylalanine, tryptophan). Those skilled in the art will appreciate that classifications of amino acid residue families other than the above can also be used. In addition, variants may have non-conservative amino acid substitutions, for example, an amino acid may be substituted with another amino acid residue having different structure or chemical property. Similar minor variations may also include amino acid deletions or insertions, or both. Guidance for determining which amino acid residues can be substituted, inserted or deleted without eliminating immunological activity can be found using computer programs well known in the art.

Functional variants may comprise truncations of the amino acid sequence at either or both the amino or carboxy termini. Functional variants of the invention may have the same or different, higher or lower binding affinities as compared to the parental binding protein, but still bind to PCSK9 or a fragment thereof. For example, a functional variant of the invention may have an increased or decreased (preferably increased) binding affinity for PCSK9 or a fragment thereof as compared to the parental binding protein. Preferably, the amino acid sequence of the variable region, including but not limited to the framework region, hypervariable region or CDR region, is modified. Typically, the light and heavy chain variable regions comprise three hypervariable regions, including three CDRs, as well as a more conserved region, i.e., the so-called framework region (FR). The hypervariable region comprises amino acid residues from the CDRs and those from the hypervariable loop. Functional variants within the scope of the invention have at least about 50% to about 99%, preferably at least about 60% to about 99%, more preferably at least about 70% to about 99%, even more preferably at least about 80% to about 99%, most preferably at least about 90% to about 99%, especially at least about 95% to about 99%, and especially at least about 97% to about 99% amino acid sequence homology to the parental binding protein described herein. Computer algorithms known to those skilled in the art, such as Gap or Bestfit, can be used to optimally align amino acid sequences for comparison and to clarify similar or identical amino acid residues. Functional variants can be obtained by altering the parental binding protein or a portion thereof using common molecular biology methods known in the art including, but not limited to, error-prone PCR, oligonucleotide-directed mutagenesis, site-directed mutagenesis, and heavy chain and/or light chain shuffling.

As a preferred embodiment of the invention, the binding protein MV072 is a monoclonal antibody. The antigen binding properties of an antibody can be described by three specific regions located in the heavy and light chain variable regions, referred to as complementary determining regions (CDRs), which divide the variable regions into four framework regions (FR), wherein the amino acid sequences of the four FRs are relatively conservative and are not directly involved in the binding reaction. These CDRs form a circular structure and are spatially close to each other by the I3-sheets formed by the intervening FRs, and the CDRs on the heavy chain and the CDRs on the corresponding light chain constitute the antigen-binding site of the antibody. The CDR regions of the anti-PCSK9 monoclonal antibodies of the invention are novel and distinct from existing anti-PCSK9 antibodies.

The monoclonal antibody of the invention is of all human origin and characterized by low immunogenicity and high safety.

As a preferred embodiment of the invention, the binding protein MV072 of the invention may also be a protein fused to IgG Fc. More preferably, the IgG1 Fc is a mutant IgG1 Fc with T255Q/M433L mutations or M257Y/S259T/T261E mutations. The inventors have found that the binding of the binding protein obtained by this modification to FcRn responsible for antibody recovery and reuse is significantly increased in an acidic environment (significantly lowered EC50 value). This predicted that the MV072 binding protein with such IgG1 Fc mutations will not be easily degraded by Endosome in vivo, its half-life in vivo will be longer, and the binding ability of the binding protein MV072 to the antigen remains unchanged.

Another aspect of the invention provides a nucleic acid molecule encoding at least one binding protein, a functional variant or immunoconjugate thereof. Such a nucleic acid molecule can be used as an intermediate for cloning, for example, in affinity maturation methods as described above. In a preferred embodiment, the nucleic acid molecule is isolated or purified. The sequence of the DNA molecule can be obtained through conventional techniques or hybridoma technology.

Once related sequences are obtained, the related sequences can be recombinantly obtained in large quantities. This is usually done by cloning the related sequences into a vector, transferring the vector into a cell, and then isolating the related sequences from the proliferated host cell by conventional methods.

In addition, related sequences can be synthesized by synthetic methods, especially when the fragment has a small length. Usually, a long fragment of a sequence can be obtained by first synthesizing a plurality of small fragments and then connecting them.

At present, it is already possible to obtain a DNA sequence encoding the binding protein MV072 of the invention (or a fragment or derivative thereof) completely by chemical synthesis. The DNA sequence can then be introduced into various existing DNA molecules (or vectors) and cells known in the art. In addition, mutations can also be introduced into the sequence of the binding protein of the invention by chemical synthesis.

The invention also relates to vectors comprising appropriate DNA sequences described above, as well as appropriate promoter(s) or control sequence(s). These vectors can be used to transform appropriate host cells to enable them to express proteins. Preferably, the vector of the invention is, for example, a plasmid expression vector containing a viral promoter, and the fusion sequence of an anti-PCSK9 monoclonal antibody heavy chain variable region (VH) and a constant region IgG2 (the constant region from human IgG2) and the fusion sequence of a light chain variable region VL and human IgLambda (the constant region from human Iglambda) are inserted into the expression vector, respectively.

Host cells can be prokaryotic cells, such as bacterial cells; or lower eukaryotic cells, such as yeast cells; or higher eukaryotic cells, such as mammalian cells. Representative examples are bacterial cells such as *Escherichia coli, Streptomyces; Salmonella typhimurium*; fungal cells such as yeast; plant cells; insect cells such as *Drosophila* S2 or Sf9; animal cells such as CHO, COST, NSO or Bowes melanoma cells, etc. Host cells particularly suitable for use in the invention are eukaryotic host cells, especially mammalian cells such as CHO cells, 293 cells.

If desired, recombinant binding proteins can be isolated and purified by various separation methods according to their physical, chemical, and other properties. These methods are well known to those skilled in the art. Examples of such methods include, but are not limited to, conventional renaturation, treatment with a protein precipitant (salting out method), centrifugation, osmotic disrupting, ultrasonication, ultracentrifugation, molecular sieve chromatography (gel filtration), adsorption chromatography, ion exchange chromatography, high performance liquid chromatography (HPLC) and various other liquid chromatography techniques and combinations thereof.

Pharmaceutical Compositions

The binding molecules of the invention are useful in the preparation of pharmaceutical compositions for the diagnosis, treatment and/or prevention of PCSK9 expression or activity disorders-related diseases.

"PCSK9 expression or activity disorders-related diseases" include conditions associated with high serum cholesterol levels. Preferably, said "PCSK9 expression or activity disorders-related diseases" include, but are not limited to, hypercholesterolemia, coronary heart disease, metabolic syndrome, acute coronary syndrome, and related conditions. PCSK9 function or the function of PCSK9 refers to any activity and function that requires involvement of PCSK9 or is aggravated or enhanced by PCSK9. PCSK9 mAb can also be used to detect and quantify PCSK9 for various diagnostic purposes.

Based on the new findings of the invention, a pharmaceutical composition for diagnosing, treating and/or preventing PCSK9 expression or activity disorders-related diseases is also provided, wherein the composition comprises an effective amount of the binding molecule of the invention, and a pharmaceutically acceptable carrier.

As used herein, the term "pharmaceutically acceptable" refers to a molecule itself and composition that do not produce disadvantageous, allergic or other adverse reactions when suitably administered to an animal or a human. As used herein, a "pharmaceutically acceptable carrier" should be compatible with the binding molecules of the invention, i.e., under normal circumstances, it can be blended with the binding molecules of the invention without substantially reducing the effect of the composition.

Particular examples of some substances which may be used as pharmaceutically acceptable carriers or components thereof are carbohydrates, such as lactose, glucose and sucrose; starches, such as corn starch and potato starch; cellulose and derivatives thereof, such as sodium carboxymethyl cellulose, ethyl cellulose and methyl cellulose; gum tragacanth powder; malt; gelatin; talc; solid lubricants, such as stearic acid and magnesium stearate; calcium sulfate; vegetable oils, such as peanut oil, cottonseed oil, sesame oil, olive oil, corn oil and cocoa butter; polyols, such as propylene glycol, glycerin, sorbitol, mannitol and polyethylene glycol; alginic acid; emulsifiers, such as Tween®; wetting agents, such as sodium lauryl sulfate; colorants; flavorings; tableting agents, stabilizers; antioxidants; preservatives; pyrogen-free water; isotonic saline solution; phosphate buffer and so on.

The pharmaceutical composition of the invention can be formulated into various dosage forms as desired, and can be administered by a physician in accordance with factors such as the type, age, body weight, and general disease condition of a patient, mode of administration, and the like. The mode of administration can be, for example, injection or other treatment ways.

The binding molecules of the invention may be used in unseparated/non-isolated or separated/isolated form. Furthermore, the binding molecules of the invention may be used alone or in a mixture comprising at least one of the binding molecules of the invention (or variants or fragments thereof). In other words, the binding molecules can be used in combination, for example as a pharmaceutical composition comprising two or more binding molecules of the invention, variants or fragments thereof. For example, the binding molecules with different but complementary activities can be combined in a single therapeutic regimen to achieve the desired prophylactic, therapeutic or diagnostic effect, but alternatively, the binding molecules with the same activity can be combined in a single therapeutic regimen to achieve the desired prophylaxis, therapeutic or diagnostic effect.

The binding molecules or pharmaceutical combinations of the invention can be tested in suitable animal model systems prior to use in humans. Such animal model systems include, but are not limited to, mice, monkeys.

Suitable dosage of the binding molecules of the invention may range, for example, from 0.001 to 100 mg/kg body weight, preferably from 0.01 to 15 mg/kg body weight. In addition, for example, one bolus or multiple divided doses may be administered over time, or the doses may be proportionally reduced or increased depending on the urgency of the treatment situation. The molecules and compositions of the invention are preferably sterile. Methods for sterilizing these molecules and compositions are well known in the art. Other molecules for diagnosis, prevention and/or treatment can be administered in a dosage regimen similar to the binding molecules of the invention. If other molecules are administered alone, they can be administered to the patient before, concurrently with, or after the administration of one or more binding molecules or pharmaceutical compositions of the invention. Accurate dosing regimens for human patients are usually selected during clinical trials.

The binding molecules of the invention can be placed in a suitable package to form a kit for use by a physician. Preferably, the kit may also include instructions for administration.

The invention also comprises a method for lowering serum cholesterol levels, treating or preventing a disease associated with high serum cholesterol levels in a patient, wherein the method comprises administering to the patient an effective amount of at least one monoclonal antibody of the invention. Preferably, the monoclonal antibody of the invention can be administered in combination with an agent that increases the availability of LDLR protein. The agent that increases the availability of LDLR protein includes atorvastatin, cerivastatin, fluvastatin, lovastatin, mevastatin, pitavastatin, rosuvastatin, simvastatin, and two or more of the agents described that increases the availability of LDLR protein may be selected.

Immunoconjugate

In another aspect, the invention comprises an immunoconjugate, which comprises at least one binding protein described herein and further comprises at least one functional molecule (e.g., a molecule of a detectable moiety/substance). The antibody and the functional molecule may form a conjugate by covalent attachment, coupling, attachment, crosslinking, or the like. The immunoconjugate of the invention may comprise more than one label. The label can also be directly bound/conjugated to the binding protein of the invention by a covalent bond. Alternatively, the label can be bound/conjugated to the binding protein by one or more linker compounds. Techniques for conjugating label and binding proteins are well known to those skilled in the art. The label of the immunoconjugate of the invention may also be a therapeutic agent.

The immunoconjugate can comprise an antibody of the invention and a detectable label. The detectable label includes, but is not limited to, a fluorescent label, a chromogenic label; e.g., enzyme, prosthetic group, fluorescent material, luminescent material, bioluminescent material, radioactive material, positron emitting metal, and non-radioactive paramagnetic metal ion. More than one label may also be included. The selection of the label used to label the antibody for detective and/or analytic and/or diagnostic purposes depends on the particular detective/analytic/diagnostic technique and/or method used, such as immunohistochemical staining (tissue) samples, flow cytometry, and the like. Labels suitable for the detective/analytic/diagnostic techniques and/or methods known in the art are well known to those skilled in the art.

Furthermore, the human binding proteins or immunoconjugates of the invention may also be attached to a solid support, which is particularly useful for in vitro immunoassays or purification of PCSK9 proteins or fragments thereof. Such a solid support can be porous or non-porous, planar or non-planar. The binding proteins of the invention can be fused to a tag sequence for purification. Examples of such tag sequence include, but are not limited to, a hexahistidine tag, hemagglutinin (HA) tag, myc tag, or flag tag. Alternatively, an antibody can be conjugated to another antibody to form an antibody heteroconjugate.

Detection Reagent and Kit

Based on the binding molecule of the invention, a reagent or kit for conveniently, rapidly and accurately detecting the level of PCSK9 in a sample to be tested can be prepared.

As used herein, the term "a sample to be tested" encompasses a variety of sample types, including biologically derived blood and other body fluid samples, solid tissue samples such as biopsy tissue samples or tissue cultures, or cells derived therefrom or progeny thereof. The term also encompasses samples that have been treated by any means after acquisition, such as treatment with reagents, dissolution, or enrichment for certain components such as proteins or polynucleotides.

Accordingly, the invention provides a detection kit for detecting PCSK9 levels in a sample to be tested, wherein the kit comprises the PCSK9 binding molecule of the invention, or an immunoconjugate of a PCSK9 binding molecule and a detectable label.

After obtaining the PCSK9 binding molecule of the invention, a detection kit for specifically detecting PCSK9 levels can be conveniently prepared.

For convenience in detection, the kit may further comprise other detection reagents or auxiliary agents in addition to the binding molecule of the invention or the immunoconjugate comprising the PCSK9 binding molecule and the detectable label, wherein the auxiliary agents are, for example, some reagents conventionally used in ELISA kits, and their characteristics and formulation methods are well known to those skilled in the art, such as developers, labels, secondary antibodies, anti-antibodies, sensitizers, etc. It will be understood by those skilled in the art that various variations of the detection kit are included in the invention as long as the binding molecule of the invention is used as reagent for recognizing PCSK9.

Furthermore, instructions may be included in the kit for indicating the method of using the reagents loaded therein.

After obtaining the binding molecules and/or kits of the invention, various immunologically related methods can be used to detect PCSK9 or its content in the sample, thereby determining whether PCSK9 expression or activity disorders-related disease is present in the donor of the sample to be tested.

The invention is further illustrated below with reference to the following examples. It is to be understood that the examples are for illustrative purposes only, and are not intended to limit the scope of the invention. The experimental methods in the following examples, when not described in detail, is contemplated to follow routine conditions in the art, for example, Sambrook et al., *Molecular Cloning: A Laboratory Manual* ($3^{rd}$ Edition, 2002), Science Press, or follow conditions suggested by manufacturer.

EXAMPLES

Example 1. Optimization and Screening of PCSK9 Monoclonal Antibodies

In order to find PCSK9 antibodies that meet the requirements, the inventors have made extensive researches and screening a whole human phage library to finally obtained two strains of monoclonal antibodies with excellent performance. The nucleic acid sequences and amino acid sequences of their variable domains are described below:

1. Monoclonal Antibody 9M284

The nucleotide sequence of the heavy chain variable region is set forth in SEQ ID NO: 1.

The amino acid sequence of the heavy chain variable region is set forth in SEQ ID NO: 2.

The amino acid sequence of each CDR region of the heavy chain:

```
HCDR1:      AFTFDSFGMH;         (SEQ ID NO: 7)

HCDR2:      LLWSDGSGEYYADSAKG;  (SEQ ID NO: 8)
and

HCDR3:      AMGAIYYYAMDV.       (SEQ ID NO: 9)
```

The nucleotide sequence of each CDR region of the heavy chain:

```
HCDR1:
                                            (SEQ ID NO: 15)
GCCTTCACCTTCGACAGCTTCGGCATGCAC;

HCDR2:
                                            (SEQ ID NO: 16)
CTGCTTTGGAGCGACGGCTCCGGCGAGTACTACGCCGACT

CCGCTAAGGGC;
and

HCDR3:
                                            (SEQ ID NO: 17)
GCGATGGGCGCCATCTACTACTACTACGCCATGGACGTG.
```

The nucleotide sequence of the light chain is set forth in SEQ ID NO: 3.

The amino acid sequence of the light chain is set forth in SEQ ID NO: 4.

The amino acid sequence of each CDR region of the light chain:

```
LCDR1:    TGTSSNIGNQFVS;    (SEQ ID NO: 10)

LCDR2:    EYNKRPS;          (SEQ ID NO: 11)
and

LCDR3:    GSWDSSLSGYV.      (SEQ ID NO: 12)
```

The nucleotide sequence of each CDR region of the light chain:

```
LCDR1:
                                            (SEQ ID NO: 18)
ACCGGCACCTCCTCCAACATCGGCAACCAATTCGTGTCC;

LCDR2:
                                            (SEQ ID NO: 19)
GAGTACAACAAGCGGCCCTCC;
and LCDR3:
                                            (SEQ ID NO: 20)
GGCTCCTGGGACTCTTCCCTGTCCGGCTATGTG.
```

2. Monoclonal Antibody 9M283

The nucleotide sequence of the heavy chain is set forth in SEQ ID NO: 5.

The amino acid sequence of the heavy chain is set forth in SEQ ID NO: 6.

The amino acid sequence of each CDR region of the heavy chain:

```
HCDR1:      AFTFDSFGMH;         (SEQ ID NO: 7)

HCDR2:      LLWSDGSDEYYADSAKG;  (SEQ ID NO: 13)
and

HCDR3:      ALGAIYSYYAMDV.      (SEQ ID NO: 14)
```

The nucleotide sequence of each CDR region of the heavy chain:

```
HCDR1:
                                            (SEQ ID NO: 15)
GCCTTCACCTTCGACAGCTTCGGCATGCAC;

HCDR2:
                                            (SEQ ID NO: 21)
CTGCTTTGGAGCGACGGCTCCGACGAGTACTACGCCGACTC

CGCTAAGGGC;
and

HCDR3:
                                            (SEQ ID NO: 22)
GCGTTGGGCGCGATCTACAGCTACTACGCCATGGACGTG.
```

The nucleotide and amino acid sequences for the light chain of monoclonal antibody 9M283 are identical to the light chain nucleotide and amino acid sequences of 9M284, and the corresponding CDR regions of 9M283 are also identical to those of 9M284.

Example 2. Preparation of PCSK9 Monoclonal Antibodies from Transfected Cells

HindIII/NotI site was added at both ends of the nucleotide sequence of the heavy chain of the aforementioned monoclonal antibody 9M284, and the nucleotide sequence was then inserted into the corresponding site of pCDNA3.1+ plasmid; and HindIII/NotI site was added at both ends of the nucleotide sequence of the light chain of the aforementioned monoclonal antibody 9M284, and the nucleotide sequence was then inserted into the corresponding site of pCDNA3.1+ plasmid. A recombinant plasmid expressing monoclonal antibody 9M284 was thus obtained.

HindIII/NotI site was added at both ends of the nucleotide sequence of the heavy chain of the aforementioned monoclonal antibody 9M283, and the nucleotide sequence was then inserted into the corresponding site of pCDNA3.1+ plasmid; and HindIII/NotI site was added at both ends of the nucleotide sequence of the light chain of the aforementioned monoclonal antibody 9M283, and the nucleotide sequence was then inserted into the corresponding site of pCDNA3.1+ plasmid. A recombinant plasmid expressing monoclonal antibody 9M283 was thus obtained.

1. Transient Transfection

The above recombinant plasmids were transiently transfected into suspended HEK293 cells by liposome method.

The obtained transfected cells were cultured in Expi293 Expression medium at 37° C., $CO_2$ 8%, and 120 rpm.

After massive culture, the transfected cells were subjected to two-stage centrifugation (first-stage centrifugation: 1,000 g for 10 min; and second-stage centrifugation: 10,000 g for 30 min) to remove cells and cell debris and obtain a supernatant. The clarified supernatant was loaded onto a Protein A affinity chromatography column and impurities were removed by three steps of rinsing (rinsing buffers sequentially used: PB 150 mM NaCl pH 6.5; 20 mM Na-citrate 1 M NaCl pH 5.5; and 20 mM Na-Citrate pH 5.5), and then the target antibody was separated and captured by pH linear elution (starting buffer A: 20 mM Na-citrate pH 5.5; and target buffer B: 20 mM Na-citrate pH 3.0). Finally, the target antibody was displaced by an ultrafiltration concentration step into a buffer of 200 mM HEPE, 100 mM NaCl, 50 mM NaOAc, pH 7.0.

2. Electrotransfection of the Cells Stably Expressing 9M284

The constructed plasmid containing the heavy chain of 9M284 (SEQ ID NO: 23, which encodes the amino acid sequence of SEQ ID NO: 24 without a leader peptide) and the light chain of 9M284 (SEQ ID NO: 25, which encodes the amino acid sequence of SEQ ID NO: 26 without a leader peptide) (total amount of 20 μs of plasmid DNA) was mixed with $1.0 \times 10^7$ host cell CHO-K1; after placed in an electroporator (Gene Pulser II), the mixture of cells and plasmid was shocked for co-transfection using an exponentially decaying wave with a voltage of 300V and a capacitance of 950 μF. The electrotransfected mixture of cells and DNA was added to a 6-well plate containing 2 mL host cell basal medium (EX-CELL® Advanced™ CHO Fed-batch Medium, Sigma, containing 6 mM L-glutamine, Sigma) and the cells were placed in a carbon dioxide incubator, incubated at 37° C. for 24 h, and then the medium was replaced with selective growth medium (EX-CELL® Advanced™ CHO Fed-batch Medium, Sigma; containing Puromycin, 20 μg/mL, GIBCO and 6 mM L-glutamine, Sigma) for a stress screening for about 3 weeks until the cell viability was restored to above 90%, and a Pool cell line containing a heavy chain and a light chain integrated into CHO-K1 genome was obtained. When the viability of Pool cells was restored to above 90%, Fed-batch culture was carried out in a 125 mL shake flask with a culture volume of 30 mL and an initial cell concentration of $0.3 \times 10^6$/mL. The feed medium (Ex-CELL Advanced CHO feed 1 (with glucose), Sigma) was fed and samples were taken to measure cell density and viability on Days 3, 5, 7, 9, 11 and 13, wherein glucose was added to 6 g/L when the glucose concentration was reduced to 3 g/L, and the culture was stopped and the antibody concentration was detected upon the viability decreased to 70% or less.

With the constructed plasmid containing the heavy chain of 9M283 (SEQ ID NO: 27, without a leader peptide, encoding the amino acid sequence of SEQ ID NO: 28) and the light chain of 9M283 (SEQ ID NO: 25, without a leader peptide, encoding the amino acid sequence of SEQ ID NO: 26), cells stably expressing 9M283 were similarly obtained.

3. Semi-Solid Cloning and ELISA Screening for Transfectants Stably Expressing 9M284

Pool cells with high antibody concentration were picked for monoclonal screening, and cell suspension containing 50-200 Pool cells was mixed with 10 mL semi-solid medium (CloneMedia CHO Growth A with L-Gln, Molecular devices), seeded on a 100 mm culture dish, and cultured in a 37° C., 5% $CO_2$ incubator for 14 days. Medium-sized cell colonies were picked out and transferred to and cultured in a 96-well plate containing 200 μL selection medium each well for 4-5 days. The cell suspension was mixed by pipetting, divided equally into two 96-well plates with fresh medium supplemented to 200 μL of culture system, wherein one plate was subjected to expansion with medium exchanged, in which the cell suspension was mixed by pipetting, 100 μL medium was taken and discarded, and 100 μL fresh medium was added, and so on; and the other plate was subjected to continuous culture without liquid exchange for 10 days, and the cell supernatant was taken for ELISA. Cell strains were selected for amplification and subcloning screening based on OD values. The preferred cell strains obtained in the first round of semi-solid screening were plated onto a 96-well cell plate at a density of 0.5 cell/well. After 7 days, the cells were observed until the single cell clones grew to a certain screening scale, and wells with only a single cell population were selected as single cell wells. The culture medium of the single cell wells in the 96-well culture plate (which can be appropriately diluted) was transferred to a coated ELISA plate, subjected to ELISA screening analysis, screened for TOP 3 single cell lines, and Fed-Batch was conducted to determine the expression level.

Example 3. Bioanalysis and Characterization of PCSK9 Monoclonal Antibodies

1. Capillary Electrophoresis (CE-SDS)

Antibodies were analyzed by capillary electrophoresis using the LabChip GXII system. The peak purity percentage and molecular weight for the samples of the PCSK9 monoclonal antibodies of the invention under reducing and non-reducing conditions were shown in Table 1 (non-reducing conditions) and Table 2 (reducing conditions).

TABLE 1

Main peak purity under non-reducing conditions

| ID# | Main Peak purity % (non-reducing conditions) | Molecular weight (kDa) |
|---|---|---|
| 9M283 | 77.1% | 178.66 |
| 9M284 | 77.6% | 178.13 |

TABLE 2

Main peak purity under reducing conditions

| ID# | Peak purity % (reducing conditions) | Molecular weight (kDa) |
|---|---|---|
| 9M283 | 35.9%, 64.2% | 37.32, 66.36 |
| 9M284 | 36.1%, 63.9% | 37.15, 66.33 |

2. Molecular Sieve Liquid Chromatography (SE-HPLC)

Monoclonal antibodies were filtered through a 0.2 μm filter (Thomson, Cat. No. 25535-100) and loaded onto a MAbPac SEC-1 column (Thermo, Cat. No. 07469620). The mobile phase buffer was 50 mM sodium phosphate, 300 mM sodium chloride, pH 6.2, at a flow rate of 0.2 ml/min. Peak value calculations were integrated using ChemStation software. The percentages of the main peak and the aggregate peak of the PCSK9 monoclonal antibodies of the invention were shown in Table 3.

TABLE 3

Analysis of main peak and aggregate peak purities

| ID# | Main peak purity % | Aggregate peak purity % |
|---|---|---|
| 9M283 | >99.9% | <0.01% |
| 9M284 | 98.0% | 2.0% |

3. Differential Scanning Calorimetry Evaluation of Protein Stability

Differential Scanning calorimetry (DSC) is a measurement technique in which the difference in the amount of heat required to increase the temperature of a sample and reference is measured as a function of temperature. Differential scanning calorimetry can be used to determine several properties of proteins, including the temperature/melting temperature at which 50% protein is Denaturated™, which is a method for assessing the stability of proteins.

Antibodies to be detected were loaded into a Nano DSC sample chamber at a concentration of 1 mg/ml, and the temperature was raised from 25° C. to 100° C. at a rate of 1° C./min. Samples were pre-scanned for 15 minutes before testing to ensure an accurate starting temperature prior to implementation. Sample values for buffer only were subtracted from the sample data; Nano DSC software was used to calculate Tm.

The results were shown in Table 4.

TABLE 4

| ID# | Tm (° C.) |
|---|---|
| 9M283 | 63° C., 74° C. |
| 9M284 | 67° C., 70° C., 76° C. |

Example 4. Characterization of Binding of the Antibodies to PCSK9

The ability of PCSK9 mAbs to bind to human, mouse or cynomolgus PCSK9 was characterized using the Octet Red 96 system (ForteBio). A kinetic-grade biosensor (Fortebio, #18-5063) of anti-human IgG Fc (AHC) was immersed in assay buffer after glycine pretreatment at pH 1.7. The PCSK9 monoclonal antibody to be detected was immobilized to the AHC biosensor at a concentration of 10 μg/ml for 120 seconds. The AHC biosensor loaded with the PCSK9 monoclonal antibody was then immersed in human PCSK9 antigen (GeneBank AX127530.1), mouse PCSK9 antigen (NCBI NM_153565.2) or cynomolgus PCSK9 antigen (NCBI NM_001112660.1) of different concentrations and buffer. The final dilution point of the analyte column only contained the detection buffer to test the non-specific binding between the buffer and the loaded biosensor. Antigen-antibody binding was detected from 80 to 120 s, and dissociation was detected from 120 to 180 s. A 60 second baseline was determined with the assay buffer. The affinity curves for anti-PCSK9 monoclonal antibodies were fitted using a 1:1 binding kinetic sensing monovalent binding model.

The kinetic analysis was shown in FIG. 1 and Table 5.

TABLE 5

| Loading ID | Sample ID | KD (M) | Kon (1/Ms) | Kdis (1/s) | Full X^2 | Full R^2 |
|---|---|---|---|---|---|---|
| 9M283 | huPCSK9 | <1.0E−12 | 3.99E+05 | <1.0E−07 | 0.024 | 0.9996 |
| 9M284 | huPCSK9 | <1.0E−12 | 3.66E+05 | <1.0E−07 | 0.0271 | 0.9995 |
| 9M283 | cynoPCSK9 | 8.00E−11 | 3.08E+05 | 2.46E−05 | 0.0146 | 0.9995 |
| 9M284 | cynoPCSK9 | <1.0E−12 | 2.98E+05 | <1.0E−07 | 0.0114 | 0.9995 |
| 9M283 | msPCSK9 | 1.40E−08 | 3.50E+05 | 5.10E−03 | 0.0366 | 0.999 |
| 9M284 | msPCSK9 | 3.00E−09 | 3.20E+05 | 9.40E−04 | 0.0636 | 0.9983 |

Example 5. Cellular LDL Uptake Assay

Human HepG2 cells were plated at a concentration of $5 \times 10^4$ cells per well of a 96-well black-walled clear plates (Costar) in DMEM medium (Mediatech, Inc) supplemented with 10% FBS and incubated at 37° C. (5% $CO_2$) overnight. Twenty μg/ml of human PCSK9 was incubated with antibody dilutions in uptake buffer (DMEM containing 10% FBS) of various concentrations or buffer alone (control) at room temperature for 1 hour to form a complex of PCSK9 and the antibody. After removing the cell supernatant, PCSK9/antibody mixture was added, followed by Dil-LDL (Invitrogen) diluted in uptake buffer at a final concentration of 8 μg/ml. After incubation at 37° C. (5% $CO_2$) for 16-18 hours, the cells were washed thoroughly with PBS, and the cellular fluorescence signal was detected through TECAN M1000 at 554 nm (excitation) and 571 nm (emission).

Figure 2:
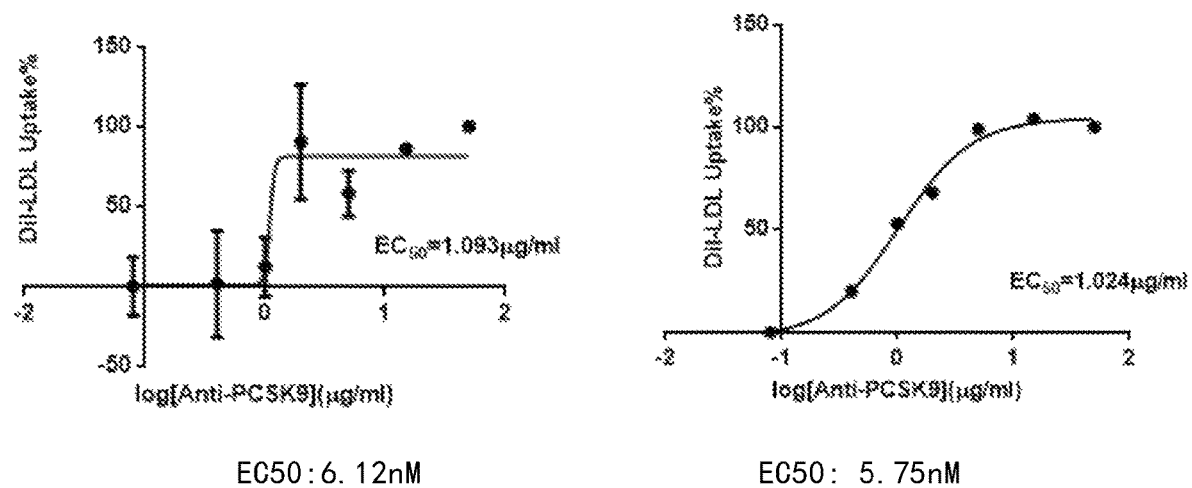
FIG. 2. Potency test of the MV072 binding proteins (i.e., monoclonal antibodies 9M283 and 9M284) in reducing cellular uptake of LDL.

The results of cellular uptake assay were shown in FIG. 2. In summary, the IC50 values of PCSK9 monoclonal antibodies were determined, and the particular values were 6.12 nM (for 9M283) and 5.75 nM (for 9M284) (FIG. 2).

The above results indicate that the antigen-binding proteins of the invention have superior ability of reducing cellular uptake of LDL.

Example 6. Effect of PCSK9 Monoclonal Antibodies on Blood LDL Levels in Hyperlipidemic Rhesus Monkeys PCSK9 monoclonal antibody 9M284 was tested in hyperlipidemic rhesus monkeys for its effect on reducing serum LDL in non-primate disease models. Four hyperlipidemic rhesus monkeys (over 7 years old) were single injected subcutaneously with vehicle (PBS+0.01% Tween 20) or a preferred PCSK9 monoclonal antibody 9M284 at a dose of 3 mg/kg on Day 0. Serum LDL levels were analyzed after fasting overnight at Day 0, 1, 3, 5, 7, 9, 11, and 14, respectively.

Figure 3:
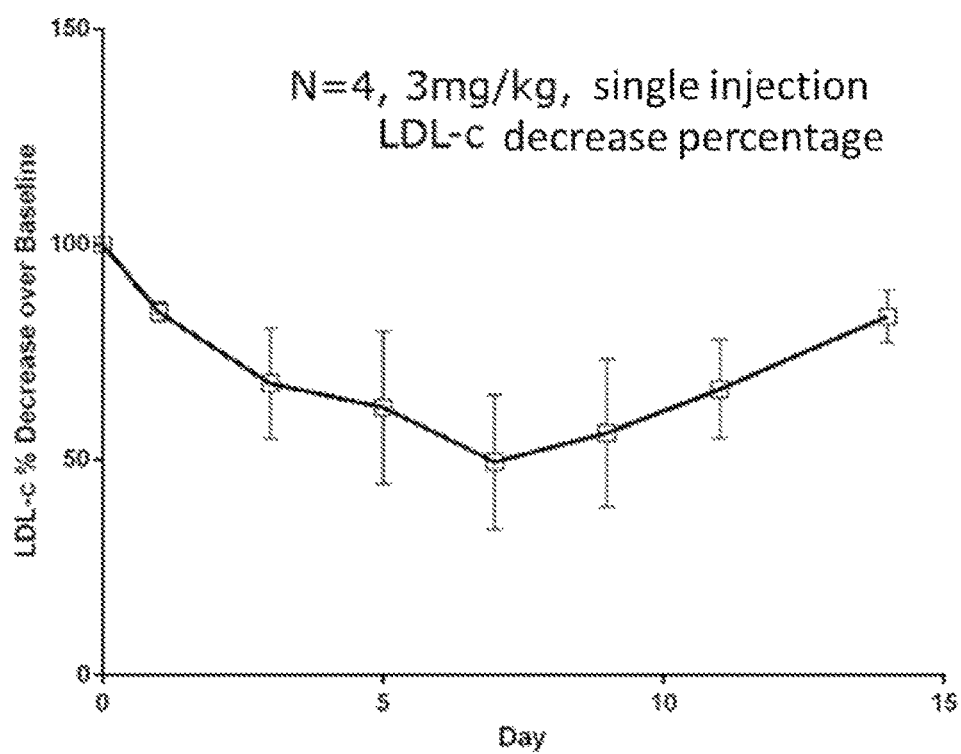
FIG. 3. Effect of preferred anti-PCSK9 antibody to serum LDL levels in rhesus monkeys with hyperlipidemia. Each group contains 4 male and female rhesus monkeys of over 7 years old, and they were injected subcutaneously with the indicated doses of preferred PCSK9 antibody or an equal volume of saline vehicle on day 0. Plasma samples were taken at the indicated time points, and the plasma LDL level was measured and compared to the serum LDL level on day 0.
Figure 4:
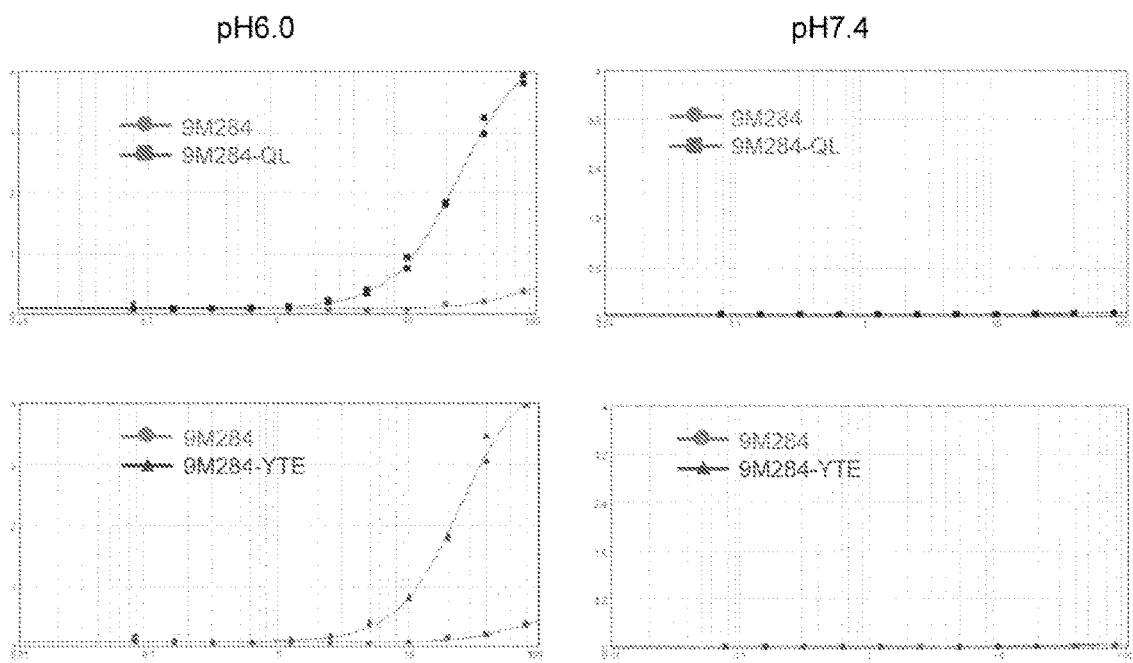
FIG. 4. ELISA binding experiments of different PCSK9 monoclonal antibodies and FcRn at pH 6.0 and pH 7.4, respectively in Example 8.

The results were shown in FIG. 3. A single injection of 3 mg/kg PCSK9 monoclonal antibody 9M284 induced a significant reduction in serum LDL (50% or more) in all 4 animals.

Similarly, the inventors also tested PCSK9 monoclonal antibody 9M283 for its effect on reducing serum LDL in vivo in hyperlipidemic rhesus monkeys. The results also demonstrated that PCSK9 monoclonal antibody 9M283 significantly reduced serum LDL levels in rhesus monkeys.

Accordingly, PCSK9 antibodies reduce serum LDL levels in non-human primate disease models.

Example 7. Prolonging the In Vivo Half-Life of PCSK9 Monoclonal Antibody 9M284 Through Fc Modification By conventional genetic engineering, the VH portion of 9M284 antibody was enzyme digested and ligated with various IgG1 Fcs (wild-type sequence as set forth in GenBank Accession No. AAD38158.1) having two or three different amino acid mutations, respectively.

The two amino acid mutations were QL mutations, the sites of the QL mutations corresponded to: position 255 of the fusion sequence of SEQ ID NO: 30, wherein T in such a site of wild type Fc has been replaced with Q after the mutation (T255Q); and position 433, wherein M in such a site in the wild-type Fc has been replaced with L after the mutation (M433L).

The three amino acid mutations were YTE mutations, the mutation sites corresponded to: position 257 of the fusion sequence of SEQ ID NO: 32, wherein M at the site before mutation has been replaced with Y after mutation (M257Y); position 259, wherein S at the site before mutation has been replaced with T after mutation (S259T); and position 261, wherein T at the site before mutation has been replaced with E after mutation (T261E). QL and YTE mutations would enhance the binding of IgG Fc in endosome to neonatal Fc receptor FcRn under acidic conditions of pH 6.0 by several times, thus reducing the degree of isolation of the antibody and FcRn in endosome (acidic pH conditions), such that the antibody could be released again into blood (pH 7.4 under normal physiological conditions, at which the antibody did not bind to FcRn), thereby achieving a longer half-life.

The heavy chain sequence of 9M284 QL is set forth in SEQ ID NO: 29 (nucleotide) and SEQ ID NO: 30 (amino acid).

The heavy chain sequence of 9M284YTE is set forth in SEQ ID NO: 31 (nucleotide) and SEQ ID NO: 32 (amino acid).

Example 8. ELISA Assay for Detection of the Binding of Different Fc Mutant PCSK9 Monoclonal Antibodies to FcRn The target antibody was diluted to 10 μg/mL with coating solution (15 mM Na$_2$CO$_3$, 35 mM NaHCO$_3$, pH 9.6), and then added to a 96-well ELISA plate at a dose of 100 μL/well and incubated at 4° C. overnight for coating. After coating, the sample wells were washed with PBST, pH 7.4 4 times, added with 300 μL/well of 4% skim milk (PBS, pH 7.4), and incubated at 25° C. for 2 hours for blocking. After blocking, the sample wells were washed 4 times with PBST, pH 7.4, added with 100 μL/well of FcRn diluted with 0.4% skim milk dissolved in PBST (pH 6.0/7.4, respectively) (initial concentration 20 μg/mL, 2-fold gradient dilution, with 11 concentration gradients in total), and incubated at 25° C. for 1.5 hours. After incubation, the sample wells were washed 4 times with PBST, pH 6.0/7.4, added with anti-His-Tag-HRP diluted in 0.4% skim milk (1/500) (pH 6.0/7.4, respectively), and incubated at 25° C. for 1 hour. After incubation, the sample wells were washed 4 times with PBST, pH 6.0/7.4, and added with 100 μL/well of TMB for development (development conditions: 25° C., 10 to 15 minutes). After development, 100 μL/well of 1 M H2SO4 was added to stop the development reaction, and the absorbance at 450 nm was read out (background correction was performed by the subtraction of the absorbance at 650 nm).

The results were shown in Table 6. The binding EC50 values of 9M284QL and 9M284YTE mutant antibodies to FcRn at pH 6.0 were 2.8 times smaller than the binding EC50 value of 9M284 to FcRn.

TABLE 6

| Sample | pH | EC50 (μg/mL) |
|---|---|---|
| 9M284 | 6.0 | 71.9 |
| 9M284-QL | 6.0 | 25.03 |
| 9M284-YTE | 6.0 | 24.32 |
| 9M284 | 7.4 | NA |
| 9M284-QL | 7.4 | NA |
| 9M284-YTE | 7.4 | NA |

Figure 5:
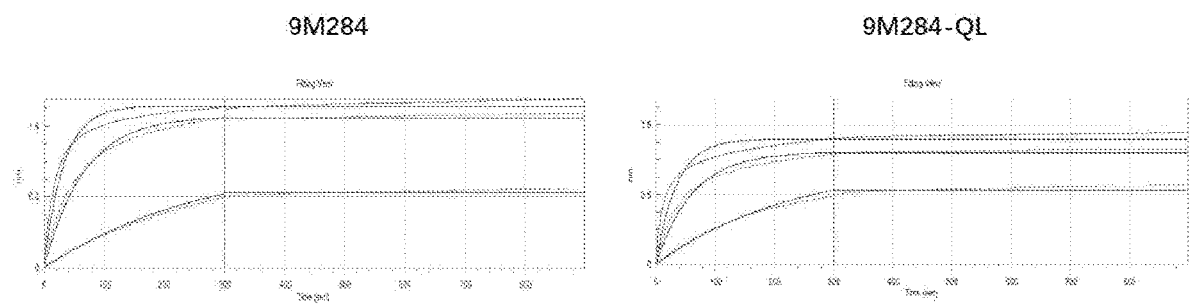
FIG. 5. Kinetic analysis results of the MV072 binding proteins (i.e., monoclonal antibodies 9M284 and 9M284QL) to human PCSK9 antigen, respectively.
Figure 6:
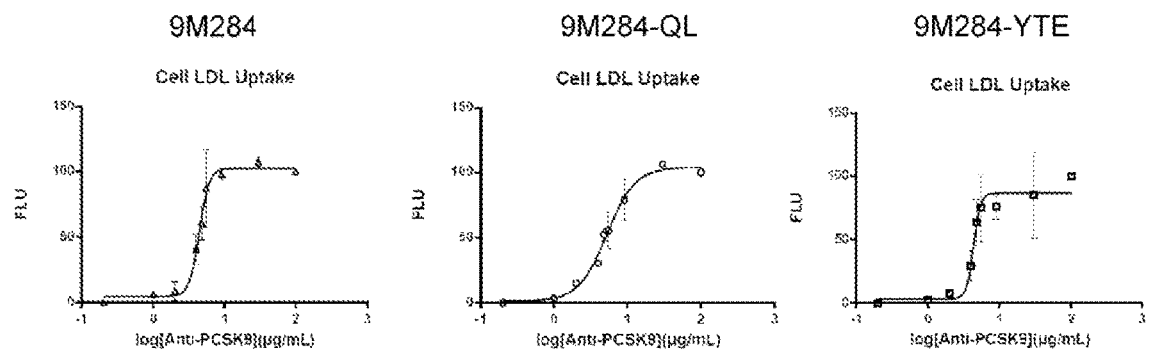
FIG. 6. Potency test of the MV072 binding proteins (i.e., monoclonal antibodies 9M284, 9M284QL, and 9M284YTE) in reducing cellular uptake of LDL.

Example 9. Affinity and Cellular Activity Assays for Long Half-Life PCSK9 Monoclonal Antibody with Modified Fc The specific experimental procedures were shown in Example 4 and Example 5. As shown in FIG. 5 and Table 7, the affinity of the long half-life antibody 9M284QL to human PCSK9 protein was substantially identical to 9M284 because the Fab region (containing VH and VL) of the engineered antibody 9M284QL was not changed compared to 9M284. As the affinity was not changed, the long half-life Fc-modified PCSK9 antibody 9M284QL, 9M284YTE and the conventional half-life antibody 9M284 had similar EC50 in the comparative test of cellular LDL uptake experiment, as shown in FIG. 6 and Table 8.

TABLE 7

| Loading ID | Sample ID | KD (M) | kon(1/Ms) | kdis(1/s) | Full X^2 | Full R^2 |
|---|---|---|---|---|---|---|
| 9M284 | PCSK9 | <1.0E−12 | 5.600E+04 | <1.0E−07 | 4.0327 | 0.9111 |
| 9M284-QL | PCSK9 | <1.0E−12 | 5.850E+04 | <1.0E−07 | 1.5254 | 0.9616 |

TABLE 8

| Sample | EC50 (ug/mL) |
|---|---|
| 9M284 | 4.519 |
| 9M284-QL | 5.28 |
| 9M284-YTE | 4.363 |

Figure 7:
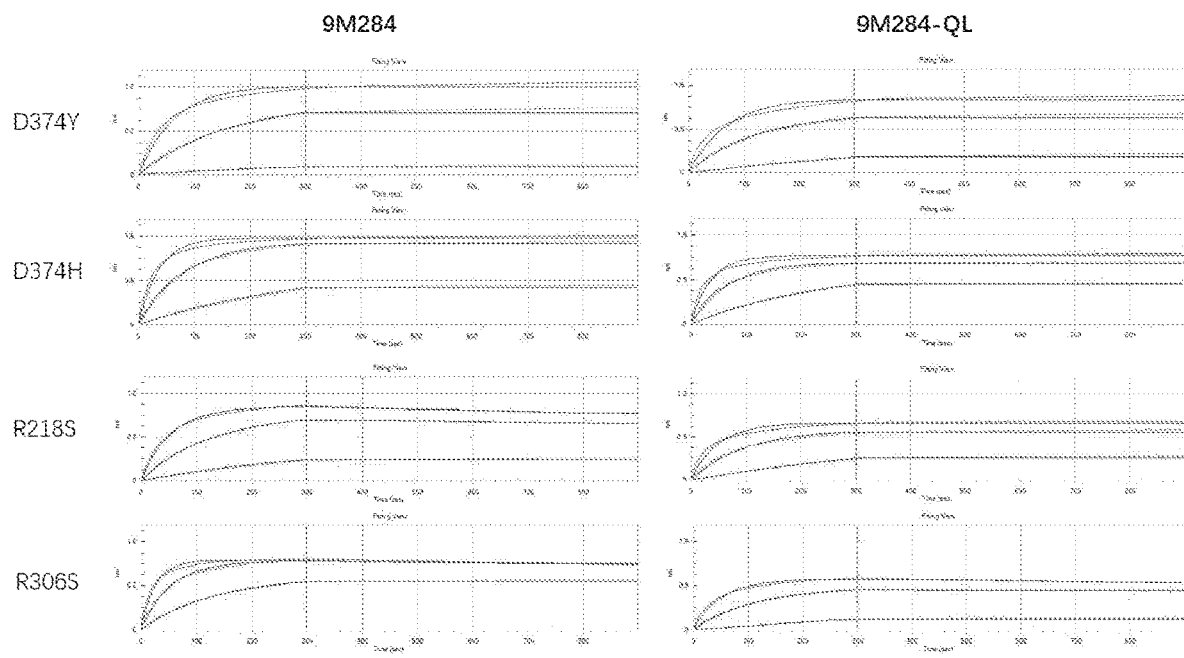
FIG. 7. Kinetic analysis results of the MV072 binding proteins (i.e., monoclonal antibodies 9M284 and 9M284QL) to different human PCSK9 antigen mutants, respectively.

Example 10. Binding Ability of Candidate PCSK9 Monoclonal Antibodies to Different PCSK9 Mutant Proteins Human PCSK9 protein had different mutants. It was reported in the literature that there were many human PCSK9 mutants associated with hyperlipidemia. The inventors selected human PCSK9 mutant proteins of R218S, R306S, D374H, and D374Y among them, wherein the ability of PCSK9 mAbs of the invention in binding to different mutant PCSK9 proteins was characterized using the Octet Red 96 system (ForteBio) as described above. The kinetic analysis was shown in FIG. 7 and Table 9, except for R306S, the affinities of other human PCSK9 protein mutants to the PCSK9 monoclonal antibodies of the invention (normal IgG and long half-life IgG forms) were of the same order of magnitude as native human PCSK9 protein. Among them, the kon-binding ability of long half-life PCSK9 monoclonal antibody 9M284-QL to PCSK9 R218S protein was three times higher than that of 9M284 antibody.

TABLE 9

| Loading ID | Protein Sample ID | KD (M) | kon(1/Ms) | kdis(1/s) | Full X^2 | Full R^2 |
|---|---|---|---|---|---|---|
| 9M284 | D374Y | <1.0E−12 | 2.184E+04 | <1.0E−07 | 3.2239 | 0.9516 |
| 9M284-QL | D374Y | <1.0E−12 | 2.967E+04 | <1.0E−07 | 1.7388 | 0.9624 |
| 9M284 | D374H | <1.0E−12 | 2.490E+04 | <1.0E−07 | 1.9488 | 0.9477 |
| 9M284-QL | D374H | <1.0E−12 | 2.689E+04 | <1.0E−07 | 0.4194 | 0.9870 |
| 9M284 | R218S | <1.0E−12 | 1.139E+04 | <1.0E−07 | 0.3261 | 0.9693 |
| 9M284-QL | R218S | <1.0E−12 | 3.649E+04 | <1.0E−07 | 1.0594 | 0.9412 |
| 9M284 | R306S | 2.398E−9 | 3.393E+04 | 8.139E−05 | 0.3701 | 0.9880 |
| 9M284-QL | R306S | 1.461E−9 | 3.180E+04 | 4.644E−05 | 0.0407 | 0.9979 |

All documents mentioned in the application are hereby incorporated by reference in their entireties as if they are incorporated separately. In addition, it is to be understood that various modifications and changes may be made to the invention by those skilled in the art after reading above disclosure, and these equivalences are also within the scope of the appended claims.

The invention claimed is:

1. A binding protein MV072 that specifically binds to PCSK9, wherein the binding protein MV072 has a light chain variable region and a heavy chain variable region, and
the amino acid sequence of the heavy chain variable region CDR1 thereof is set forth in SEQ ID NO: 7;
the amino acid sequence of the heavy chain variable region CDR2 thereof is set forth in SEQ ID NO: 8 or SEQ ID NO: 13;
the amino acid sequence of the heavy chain variable region CDR3 thereof is set forth in SEQ ID NO: 9 or SEQ ID NO: 14;
the amino acid sequence of the light chain variable region CDR1 thereof is set forth in SEQ ID NO: 10;
the amino acid sequence of the light chain variable region CDR2 thereof is set forth in SEQ ID NO:11; and
the amino acid sequence of the light chain variable region CDR3 thereof is set forth in SEQ ID NO: 12.

2. The binding protein MV072 that specifically binds to PCSK9 according to claim 1, which is selected from the group consisting of:
(a) the amino acid sequences of CDR1, CDR2 and CDR3 in the heavy chain variable region are set forth in SEQ ID NO: 7, SEQ ID NO: 8, and SEQ ID NO: 9, respectively; and the amino acid sequences of CDR1, CDR2 and CDR3 in the light chain variable region are set forth in SEQ ID NO: 10, SEQ ID NO: 11, and SEQ ID NO: 12, respectively; or
(b) the amino acid sequences of CDR1, CDR2 and CDR3 in the heavy chain variable region are set forth in SEQ ID NO: 7, SEQ ID NO: 13, and SEQ ID NO: 14, respectively; and the amino acid sequences of CDR1, CDR2 and CDR3 in the light chain variable region are set forth in SEQ ID NO: 10, SEQ ID NO: 11, and SEQ ID NO: 12, respectively.

3. The binding protein MV072 that specifically binds to PCSK9 according to claim 1, wherein the amino acid sequence of the heavy chain variable region thereof is set forth in SEQ ID NO: 2 or SEQ ID NO: 24, and the amino acid sequence of the light chain variable region thereof is set forth in SEQ ID NO: 4 or SEQ ID NO: 26; or
the amino acid sequence of the heavy chain variable region thereof is set forth in SEQ ID NO: 6 or SEQ ID NO: 28, and the amino acid sequence of the light chain variable region thereof is set forth in SEQ ID NO: 4 or SEQ ID NO: 26.

4. The binding protein MV072 that specifically binds to PCSK9 according to claim 1, wherein the heavy chain variable region thereof is further linked to IgG1 Fc.

5. The binding protein MV072 that specifically binds to PCSK9 according to claim 4, wherein the IgG1 Fc is:
a mutant IgG1 Fc carrying T255Q and M433L mutations and having the amino acid sequence set forth in SEQ ID NO: 30; or
a mutant IgG1 Fc carrying M257Y, S259T and T261E mutations and having the amino acid sequence set forth in SEQ ID NO: 32.

6. The binding protein MV072 that specifically binds to PCSK9 according to claim 5, wherein the amino acid sequence obtained by ligating the heavy chain variable region with IgG1 Fc is set forth in SEQ ID NO: 30 or SEQ ID NO: 32.

7. A pharmaceutical composition, wherein the pharmaceutical composition comprises:
an effective amount of the binding protein MV072 that specifically binds to PCSK9 according to claim 1; and
a pharmaceutically acceptable carrier.

8. A kit for treating and/or preventing a condition associated with high serum cholesterol levels, wherein the kit comprises:
the binding protein MV072 that specifically binds to PCSK9 according to claim 1 or
the pharmaceutical composition according to claim 7; and
instructions for administration.

9. An immunoconjugate, wherein the immunoconjugate comprises:
the binding protein MV072 that specifically binds to PCSK9 according to claim 1; and
a detectable label.

10. The immunoconjugate according to claim 9, wherein the detectable label comprises one or more of a fluorescent label and a chromogenic label.

11. A detection kit for detecting the level of PCSK9, wherein the detection kit comprises:
the binding protein MV072 that specifically binds to PCSK9 according to claim 1; and
a detection label.

12. The detection kit for detecting the level of PCSK9 according to claim 11, wherein the detection kit further comprises: the immunoconjugate according to claim 9.

* * * * *